(12) United States Patent
Allen et al.

(10) Patent No.: US 7,265,246 B2
(45) Date of Patent: Sep. 4, 2007

(54) INDANE DERIVATES AS MUSCARINIC RECEPTOR AGONISTS

(75) Inventors: Jennifer Rebecca Allen, Indianapolis, IN (US); Stephen Andrew Hitchcock, Westlake Village, CA (US); Bin Liu, Fishers, IN (US); William Wilson Turner, Lawai, HI (US)

(73) Assignee: Eli Lilly and Company, Indianapolis, IN (US)

( * ) Notice: Subject to any disclaimer, the term of this patent is extended or adjusted under 35 U.S.C. 154(b) by 90 days.

(21) Appl. No.: 10/560,757

(22) PCT Filed: Jun. 23, 2004

(86) PCT No.: PCT/US2004/019094

§ 371 (c)(1),
(2), (4) Date: Dec. 14, 2005

(87) PCT Pub. No.: WO2005/009941

PCT Pub. Date: Feb. 3, 2005

(65) Prior Publication Data

US 2007/0060587 A1    Mar. 15, 2007

Related U.S. Application Data

(60) Provisional application No. 60/484,696, filed on Jul. 3, 2003.

(51) Int. Cl.
*C07C 233/65* (2006.01)
*A61K 31/165* (2006.01)

(52) U.S. Cl. .................. 564/186; 564/184; 514/617
(58) Field of Classification Search ............... 564/184, 564/186; 514/617
See application file for complete search history.

(56) References Cited

U.S. PATENT DOCUMENTS

2005/0054729 A1 *  3/2005  Wohlfart et al. ............ 514/617

FOREIGN PATENT DOCUMENTS

| WO | WO97/25983  | 7/1997 |
| WO | WO99/04778  | 2/1999 |
| WO | WO03/027061 | 4/2003 |

\* cited by examiner

*Primary Examiner*—Shailendra Kumar
(74) *Attorney, Agent, or Firm*—Danica Hostettler

(57) ABSTRACT

The present invention relates to compounds of Formula I: I which are agonists of the M-1 muscarinic receptor

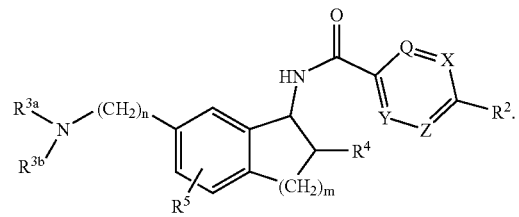

15 Claims, No Drawings

INDANE DERIVATES AS MUSCARINIC RECEPTOR AGONISTS

This is the national phase application, under 35 U.S.C. § 371, for PCT/US2004/019094, filed 23 Jun. 2004, which, claims the benefit, under 35 U.S.C. 119(e), of U.S. Provisional Application No. 60/484,696 filed on 3 Jul. 2003.

The present invention relates to the field of pharmaceutical and organic chemistry and provides compounds that are active at the muscarinic receptors.

The compounds of the present invention are muscarinic agonists. More specifically, the compounds of the present invention are selective agonists of the muscarinic M-1 receptor. As such, they are useful for treating a variety of disorders of the central nervous system and other body systems. These disorders include cognitive disorders, ADHD, obesity, Alzheimer's disease, psychoses including schizophrenia, and for alleviation of intraocular pressure such as that found in glaucoma.

Certain indane-like compounds are described as useful for treating conditions associated with malfunctioning of the muscarinic cholinergic system in PCT Publication Nos. WO 97/25983, published 24 Jul. 1997; WO 99/04778, published 4 Feb. 1999; and WO 03/027061, published 3 Apr. 2003.

The present invention provides compounds of Formula I:

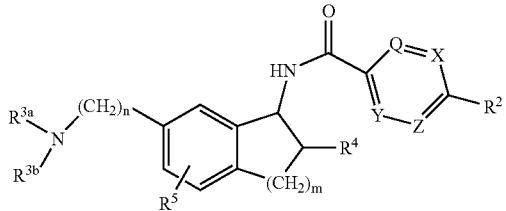

wherein

Q, X, Y, and Z are independently selected from the group consisting of $CR^1$ and N, provided that no more than two of Q, X, Y, and Z are N and at least two of Q, X, Y, and Z are CH; or Y is CH, Z is CH, and the moiety "Q=X" represents "S" to form a thiophene ring;

$R^1$ is independently at each occurrence selected from the group consisting of hydrogen, halogen, $C_1$-$C_4$ alkoxy, and $C_1$-$C_4$ alkyl;

$R^2$ is selected from the group consisting of halogen; $C_1$-$C_4$ alkoxy; $C_1$-$C_4$ alkyl; $C_3$-$C_8$ cycloalkyl; cyano; trifluoromethyl; pyridinyl optionally substituted with one to two substituents independently selected from the group consisting of halogen, $C_1$-$C_4$ alkoxy, and $C_1$-$C_4$ alkyl; thienyl optionally substituted with one substituent selected from the group consisting of halogen, $C_1$-$C_4$ alkoxy, and $C_1$-$C_4$ alkyl; phenyl optionally substituted with from one to three substituents independently selected from the group consisting of halogen, $C_1$-$C_4$ alkoxy, $C_1$-$C_4$ alkyl, trifluoromethyl, and cyano; and pyrrolyl optionally substituted with one to two substituents independently selected from the group consisting of halogen, $C_1$-$C_4$ alkoxy, and $C_1$-$C_4$ alkyl;

$R^{3a}$ is a radical of the formula (Z')-(Y')$_q$-(X')$_p$- wherein

X' is selected from the group consisting of $C_1$-$C_4$ alkandiyl and

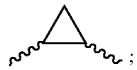

Y' is selected from the group consisting of O and S; and

Z' is selected from the group consisting of $C_1$-$C_4$ alkyl; $C_3$-$C_8$ cycloalkyl optionally substituted with one to three substituents independently selected from the group consisting of halogen, $C_1$-$C_4$ alkoxy, $C_1$-$C_4$ alkyl, trifluoromethyl, cyano, and nitro; phenyl optionally substituted with one to three substituents independently selected from the group consisting of halogen, $C_1$-$C_4$ alkoxy, $C_1$-$C_4$ alkyl, trifluoromethyl, cyano, and nitro; heteroaryl optionally substituted with one or two substituents independently selected from the group consisting of halogen, $C_1$-$C_4$ alkoxy, and $C_1$-$C_4$ alkyl; and heterocycle optionally substituted with one or two substituents independently selected from the group consisting of halogen, $C_1$-$C_4$ alkoxy, and $C_1$-$C_4$ alkyl;

p is zero or one;

q is zero or one;

provided that when p is zero, q is zero;

$R^{3b}$ is selected from the group consisting of hydrogen, $C_1$-$C_4$ alkyl, and benzyl;

or $R^{3a}$ and $R^{3b}$ are taken together with the nitrogen with which they are attached to form a heterocycle optionally substituted with one or two substituents independently selected from the group consisting of halogen, $C_1$-$C_4$ alkoxy, and $C_1$-$C_4$ alkyl;

$R^4$ is selected from the group consisting of hydrogen, hydroxy, and fluoro;

$R^5$ is selected from the group consisting of hydrogen, halogen, $C_1$-$C_4$ alkoxy, and $C_1$-$C_4$ alkyl;

m is one or two;

n is one or two;

or pharmaceutically acceptable addition salts thereof.

The present invention also provides pharmaceutical compositions, comprising a compound of Formula I and a pharmaceutically acceptable diluent.

Because the compounds of Formula I are agonists of the M-1 muscarinic receptor, the compounds of Formula I are useful for the treatment of a variety of disorders associated with muscarinic receptors, including: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia), dementia (including Alzheimer's disease, AIDS-induced dementia, vascular dementia, and dementia lacking distinctive histology), Parkinson's disease, and Huntington's Chorea. Also, the present compounds are useful for treating chronic colitis, including Crohn's disease. Additionally, the present compounds are useful for the treatment of pain (including acute pain and chronic pain), xerostomia (dry mouth), Lewy body disease (including diffuse Lewy body disease), aphasia (including primary aphasia and primary aphasia syndromes), and hypotensive syndromes.

In another embodiment the present invention provides methods of treating disorders associated with muscarinic receptors, comprising: administering to a patient in need thereof an effective amount of a compound of Formula I. That is, the present invention provides for the use of a compound of Formula I or a pharmaceutical composition thereof for the manufacture of a medicament for the treatment of disorders associated with muscarinic receptors. The present invention also provides a compound of Formula I for use in therapy.

As used herein, the following terms have the meanings indicated:

The term "halo" or "halogen" refers to a chloro, fluoro, bromo or iodo atom.

The term "$C_1$-$C_4$ alkyl" refers to a straight or branched alkyl chain having from one to four carbon atoms, examples of which include methyl, ethyl, n-propyl, iso-propyl, n-butyl, sec-butyl, iso-butyl, and t-butyl. The term "$C_1$-$C_4$ alkandiyl" refers to a straight-or branched-chain alkandiyl having from one to four carbon atoms in total, examples of which include methylene, ethylene, tetramethylene, 1-methylpropan-1,3-diyl, 2-methylpropan-1,3-diyl, and butan-2,3-diyl. The term "$C_3$-$C_8$ cycloalkyl" refers to cyclopropyl, cyclobutyl, cyclopentyl, cyclohexyl, cycloheptyl, and cyclooctyl.

The term "$C_1$-$C_4$ alkoxy" refers to a straight or branched alkyl chain having from one to four carbon atoms attached to an oxygen atom, examples of which include methoxy, ethoxy, n-propoxy, iso-propoxy, n-butoxy, iso-butoxy, sec-butoxy, and t-butoxy.

The term "heteroaryl" is taken to mean a stable unsaturated five- or six-membered ring containing from 1 to 2 heteroatoms selected from the group consisting of nitrogen, oxygen and sulfur. Examples of heteroaryl include pyridinyl, pyrimidinyl, pyrazinyl, pyrrolyl, oxazolyl, isoxazolyl, imidazolyl, thiazolyl, pyridazinyl, furyl, thienyl, and the like. Preferred heteroaryl groups are thienyl, pyridinyl, and furyl.

The term "heterocycle" is taken to mean a stable saturated five- or six-membered ring containing from 1 to 3 heteroatoms selected from the group consisting of nitrogen, oxygen and sulfur. Examples of heterocycle include pyrrolidinyl, piperidinyl, piperazinyl, tetrahydrofuryl, morpholino, and the like The compounds of the present invention form pharmaceutically acceptable acid addition salts with a wide variety of organic and inorganic acids and include the physiologically acceptable salts which are often used in pharmaceutical chemistry. Such salts are also part of this invention. A "pharmaceutically-acceptable addition salt" is formed from a pharmaceutically-acceptable acid as is well known in the art. Such salts include the pharmaceutically acceptable salts listed in Journal of Pharmaceutical Science, 66, pg. 2-19 (1977), which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

The present invention includes the stereoisomers and tautomers of the compounds of Formula I. Herein, the Cahn-Prelog-Ingold designations of (R)- and (S)- and the cis and trans designation of relative stereochemistry are used to refer to specific isomers and relative stereochemistry.

As with any group of pharmaceutically active compounds, some groups are preferred in their end use application. The following paragraphs define preferred classes.

a) When $R^4$ is not hydrogen, compounds which have trans stereochemistry at the 1- and 2-position are preferred.

b) When $R^4$ is not hydrogen, compounds which have the trans stereochemistry at the 1- and 2-position shown below are more preferred.

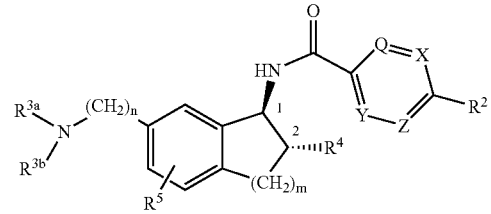

c) $R^5$ is hydrogen.
d) $R^4$ is hydroxy.
e) m is one.
f) $R^5$ is hydrogen, $R^4$ is hydroxy, and m is one.
g) Q, X, Y, and Z are each $CR^1$ provided that at least two of Q, X, Y, and Z are CH.
h) $R^1$ is hydrogen.
i) $R^1$ is halogen.
j) $R^1$ is fluoro.
k) Q, X, Y, and Z are each CH.
l) One of Q, X, Y, and Z is CF and the others are CH.
m) Q is CF and X, Y, and Z are each CH.
o) $R^2$ is phenyl optionally substituted with from one to three substituents independently selected from the group consisting of halogen, $C_1$-$C_4$ alkoxy, $C_1$-$C_4$ alkyl, trifluoromethyl, and cyano.
p) $R^2$ is phenyl.
q) $R^{3a}$ radical wherein X' is $C_1$-$C_4$ alkandiyl and p is one.
r) $R^{3a}$ radical wherein Y' is O and q is one.
s) $R^{3a}$ radical wherein Y' is S and q is one.
t) $R^{3a}$ radical wherein Z' is phenyl optionally substituted with one to three substituents independently selected from the group consisting of halogen, $C_1$-$C_4$ alkoxy, $C_1$-$C_4$ alkyl, trifluoromethyl, cyano, and nitro.
u) $R^{3a}$ radical wherein Z' is $C_1$-$C_4$ alkyl.
v) $R^{3a}$ radical wherein X' is $C_1$-$C_4$ alkandiyl, Y' is O, Z' is $C_1$-$C_4$ alkyl, p is one, and q is one.
w) $R^{3a}$ radical wherein X' is $C_1$-$C_4$ alkandiyl, Y' is S, Z' is $C_1$-$C_4$ alkyl, p is one, and q is one.
x) $R^{3a}$ radical wherein X' is $C_1$-$C_4$ alkandiyl; Y' is O; Z is phenyl optionally substituted with one to three substituents independently selected from the group consisting of halogen, $C_1$-$C_4$ alkoxy, $C_1$-$C_4$ alkyl, trifluoromethyl, cyano, and nitro; p is one; and q is one.
y) $R^{3a}$ radical wherein X' is $C_1$-$C_4$ alkandiyl; Y' is S; Z' is phenyl optionally substituted with one to three substituents independently selected from the group consisting of halogen, $C_1$-$C_4$ alkoxy, $C_1$-$C_4$ alkyl, trifluoromethyl, cyano, and nitro; p is one; and q is one.

z) $R^{3b}$ is hydrogen.
aa) $R^{3b}$ is $C_1$-$C_4$ alkyl.
bb) n is one.

The preceding paragraphs may be combined to define additional preferred classes of compounds.

One of ordinary skill in the art will appreciate that the particular order of steps may vary depending on the particular compound being synthesized, the starting compound, and the relative lability of the substituted moieties. The compounds of the present invention can be prepared by a variety of procedures, some of which are illustrated below.

fractional crystallization of diasteriomeric acid addition salts. It is expected that a wide variety of such salts are suitable for this purpose. In practice, isomers of mandelic acid have been found to be particularly useful.

For example, the compound of Formula (1) is contacted with the selected acid. Generally, from about 0.4 molar equivalents to a large excess of the selected acid can be used with about 0.4 to 1.5 molar equivalents being preferred and with about 0.5 to 1.1 molar equivalents being more preferred. The resolution is typically carried out by crystallizing the acid addition salt from a solution. In particular, solvents

SCHEME A

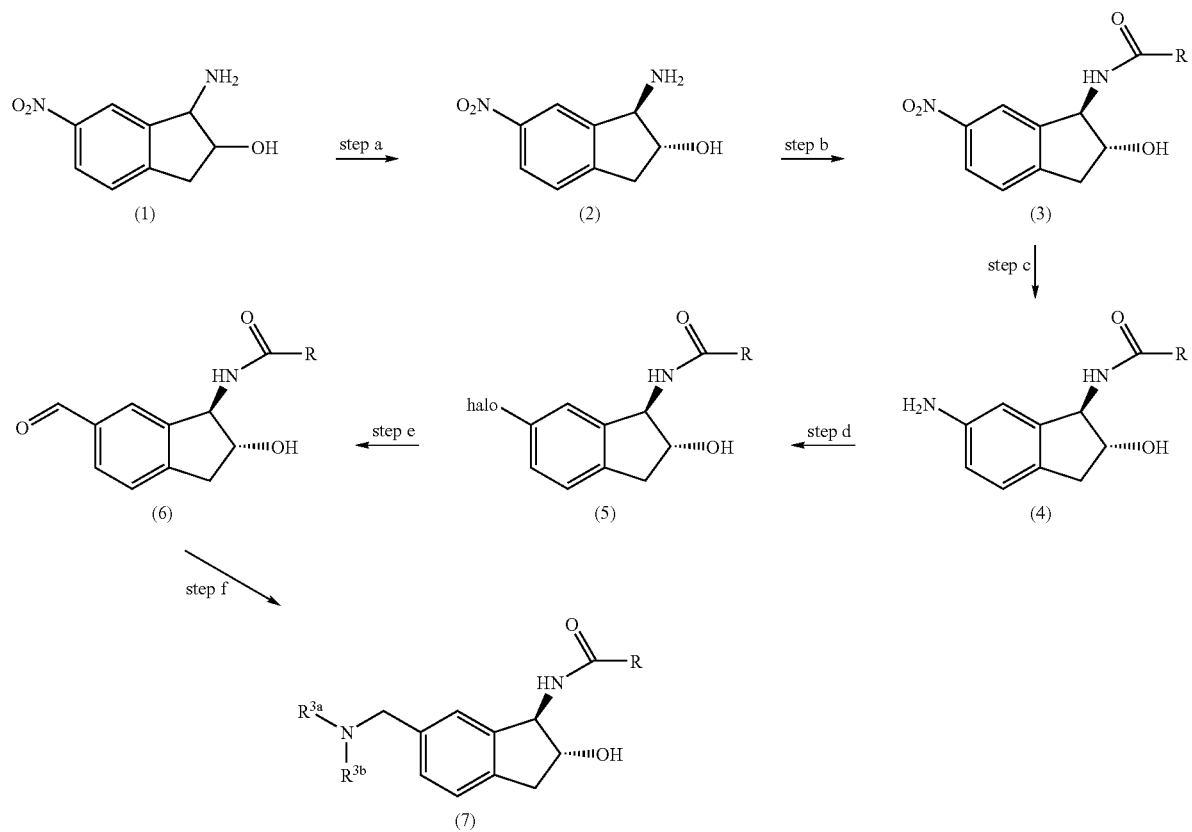

In Scheme A, step a, the compound of Formula (1) is resolved to give a substantially pure compound of Formula (2). The compound of Formula (1) is readily prepared by methods well known and appreciated in the art, such as those found in PCT Publication Nos. WO 97/125983, published 24 Jul. 1997; and WO 99/04778, published 4 Feb. 1999. As used herein the term "substantially pure" refers to enantiomeric purity. The desired stereochemistry in final compounds of Formula I may be conveniently introduced in Scheme A, step a, by resolution of compounds of Formula (1). Further processing of resolved compounds of Formula (1), via steps b, c, d, e, f, g, and optional step h, described infra, will result in substantially pure compounds of Formula I. Substantially pure compounds of Formula I can be prepared which are greater than 80%, preferably greater than 90%, more preferably greater than 95%, most preferably greater than 97% enantiomerically pure. The compound of Formula (1) can be resolved by chiral chromatography or by such as lower alcohols, including methanol are useful. It may be advantageous to use small amounts of water with the selected solvent(s) in order to carry out the resolution in a reasonable volume. The use of an anti-solvent may also be advantageous. As used herein, the term "anti-solvent" refers to a solvent in which the salt is significantly less soluble compared to the other selected solvent(s). Preferably, when an anti-solvent is used it is miscible with the other selected solvent(s). Suitable anti-solvents include ethers, such as diethyl ether, methyl t-butyl ether, and the like, and lower alkyl acetates, such as methyl acetate, ethyl acetate, isopropyl acetate, propyl acetate, iso-butyl acetate, sec-butyl acetate, butyl acetate, amyl acetate, iso-amyl acetate, and the like, and alkanes, such as pentane, hexane, heptane, cyclohexane, and the like. When the racemic mixture is used, care should be taken in using an anti-solvent to avoid crystallization of the salt of the undesired diastereomeric salt.

Typically, the crystallization is carried out at initial temperatures of about 40° C. to reflux temperature of the selected solvent(s). The mixture is then cooled to give the salt. Seeding may be advantageous. Preferably the crystallization solution is cooled slowly. The crystallization is most conveniently cooled to temperatures of ambient temperature to about −20° C. The salt can be collected using techniques that are well known in the art, including filtration, decanting, centrifuging, evaporation, drying, and the like. The compound of Formula (2) can be used directly as the acid addition salt of the selected acid. Alternately, before use the compound of Formula (2) can be isolated as another acid addition salt after acid exchange or can by isolated as the base by extraction under basic conditions as is well known and appreciated in the art.

As is readily apparent to one skilled in the art the depicted compound of Formula (2) is of the trans configuration at the 1- and 2-positions of the indane nucleus. C is compounds are readily prepared from such trans compounds by protection of the amine, inversion of the hydroxy center, followed by deprotection as needed. There are numerous methods which allow for inversions of hydroxy centers, such as by Mitsunobu reaction with suitable carboxylic acids, including acetic acid and benzoic acid, followed by hydrolysis. Alternately, an appropriately resolved amino-indanol may be selectively nitrated to produce a compound of Formula (2). For example, the resolved amino-indanol may be introduced to a nitrating agent, such as nitric acid or sodium nitrate. This reaction may be conducted in the presence of a strong acid, such as trifluoroacetic acid or sulfuric acid. Subsequently, the reaction may be neutralized with an appropriate base such as sodium hydroxide. Methods of nitration are well known in the art; see, for example, Organic Chemistry, Morrison & Boyd, 5th Ed (Allyn & Bacon, Inc.).

Reaction Scheme A, step b, depicts the formation of a compound of Formula (3). It is understood that the compound of Formula (3) can be one in which R is a group as desired in the final product of Formula I as defined above. R may also combine with the carbonyl to form a protecting group, such as t-BOC, which can be later removed before incorporation of an R group as desired in the final product of Formula I. The selection and use of suitable protecting groups is well known and appreciated in the art (Protecting Groups in Organic Synthesis, Theodora Greene (Wiley-Interscience)).

For example, where R is a group as desired in the final product, the coupling reaction depicted in step b is carried out using the appropriate acid or the acid halide derived therefrom. Appropriate acids include various substituted benzoic acids and acid halides, heteroaryl acids and acid halides, and various biaryl carboxylic acids and acid halides. Examples include biphenyl carboxylic acid and 3-fluorobiphenyl-4-carboxylic acid.

For example, the compound of Formula (2) is contacted with an appropriate acid to give a compound of Formula (3). Such coupling reactions are common in peptide synthesis and synthetic methods used therein can be employed. For example, well known coupling reagents, such as resin-bound reagents and carbodiimides with or without the use of well-known additives such as N-hydroxysuccinimide, 1-hydroxybenzotriazole, etc. can be used to facilitate this acylation. The reaction is conventionally conducted in an inert aprotic polar diluent such as dimethylformamide (DMF), methylene chloride (dichloromethane), chloroform, acetonitrile, tetrahydrofuran (THF), and the like. Typically the reaction is carried out at temperatures of from about 0° C. to about 60° C. and typically require from about 1 to about 24 hours. Upon reaction completion, the product of Formula (3) is recovered by conventional methods including extraction, precipitation, chromatography, filtration, trituration, crystallization and the like.

Alternatively, for example, the compound of Formula (2) is contacted with an acid halide of an appropriate acid to give a compound of Formula (3). Such acid halides are commercially available or readily prepared from the corresponding acids by methods well known in the art, such as by the action of phosphorous trichloride, phosphorous tribromide, phosphorous oxychloride, phosphorous pentachloride, thionyl chloride, thionyl bromide, or oxalyl chloride, with or without a small amount of dimethylformamide, in an inert solvent such as, toluene, methylene chloride, or chloroform; at temperatures of from about 0-80° C. The reaction is typically carried out for a period of time ranging from 1 hour to 24 hours. The acid halide can be isolated and purified or can often be used directly, that is, with or without isolation and/or purification. The coupling reactions generally use a suitable base to scavenge the acid generated during the reaction. Suitable bases include, by way of example, sodium hydroxide, potassium hydroxide, pyridine, triethylamine, N,N-diisopropylethylamine, N-methylmorpholine, and the like. The reaction is conventionally conducted in a solvent such as methylene chloride, chloroform, tetrahydrofuran and the like, or under Schotten-Baumann conditions in a solvent mixture such as methylene chloride, ethyl acetate, toluene and water. Typically the coupling reaction is carried out at temperatures of from about −20° C. to about 80° C. and typically require from about 1 to about 24 hours. Upon reaction completion, the product of Formula (3) is recovered by conventional methods including extraction, precipitation, chromatography, filtration, trituration, crystallization and the like.

Reaction Scheme A, step c, depicts the reduction of a nitro group to give a compound of Formula (4). Such reductions can be carried out by a variety of methods that are well known in the art.

For example, a compound of Formula (3) may be hydrogenated over a catalyst, such as palladium-on-carbon, to give a compound of Formula (4). Such hydrogenations are generally carried out in a solvent and a variety of solvents are suitable, for example methanol, ethanol, isopropanol, tetrahydrofuran, or ethyl acetate or mixtures thereof. The hydrogenation may be performed at an initial hydrogen pressure of 20-180 psi (137-1241 kPa). The reaction is typically carried out at temperature of about 0° C. to about 60° C. The reaction typically requires 1 hour to 3 days. The product can be isolated and purified by techniques well known in the art, such as filtration, extraction, evaporation, trituration, precipitation, chromatography, and recrystallization.

Reaction Scheme A, step d, depicts the conversion of the amine group to a halo group such as iodo. The conversion of anilines to aryl halides can be accomplished, for example, via diazotization with nitrous acid or isoamyl nitrite, followed by treatment with reagents such as diiodomethane or iodine, as described in Larock, Comprehensive Organic Transformations, pg. 345-47 (1989).

Reaction Scheme A, step e, depicts the formation of a compound of formula (6). Aryl halides can be converted to aldehydes by methods such as transition metal catalyzed couplings with carbon monoxide, such as described in Larock, Comprehensive Organic Transformations, pg. 678-79 (1989).

Reaction Scheme A, step f, depicts the formation of a compound of formula (7). The conversion of an aldehyde to an amine is well known and appreciated in the art. For example, aldehydes can be converted to amines by treatment with an amine and a reducing agent, such as described in Larock, Comprehensive Organic Transformations, pg. 421-28 (1989).

One of ordinary skill in the art will appreciate that the manner and particular order of steps may vary. For example, where R combines with the carbonyl to form a protecting group in step b, a compound of formula (5) may be deprotected and steps e and f may be followed to provide a compound of Formula I. Alternatively, where R is a group as desired in the final product of Formula I, a compound of formula (5) may be converted to a a compound of formula (7) where $R^{3a}$ and $R^{3b}$ are both hydrogen, then may be substituted at the amine to provide a compound of Formula I.

Some compounds of Formula I are intermediates for other final compounds of Formula I. For example, when $R^2$ is iodo, another reagent, for example, 2-(tributylstannyl) thiophene or 2-(tributylstannyl)pyridine, may be used to displace iodo as a leaving group and substitute a different $R^2$ group as desired in the final product.

In Scheme A, optional step g, not shown, an acid addition salt of a compound of Formula I is formed using a pharmaceutically-acceptable acid. The formation of acid addition salts is well known and appreciated in the art.

The compounds of Formula I in which $R^4$ is hydrogen are prepared from amine protected compounds of Formula (3) or from amine protected compounds of Formula (2) by deoxygenation. Such deoxygenation reactions are readily carried out using procedures well known in the art, described, for example, by Larock, Comprehensive Organic Transformations, pg. 44-52 (1999).

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "M" refers to molar or molarity; "mmol" refers to millimole or millimoles; "g" refers to gram or grams; "mL" refers milliliter or milliliters; "mp" refers to melting point; "brine" refers to a saturated aqueous sodium chloride solution; etc. In the $^1$H NMR, all chemical shifts are given in δ, unless otherwise indicated.

COUPLING PROCEDURES

Method A

2'-Chlorobiphenyl-4-carboxylic acid

Combine methyl-4-bromobenzoate (1.0 g, 4.65 mmol), 2-chlorophenylboronic acid (799 mg, 5.1 mmol), Pd(OAc)$_2$ (51 mg, 0.46 mmol) and sodium carbonate (1.5 g, 13.9 mmol) in dimethylformamide (20 mL) and water (2.0 mL) with stirring. Purge the reaction mixture with argon, add triphenylphosphine (61 mg, 0.23 mmol) and purge again with argon. Place the sealed reaction in an oil bath maintained at 80° C. and allow to stir for 1 hour. Cool the reaction to room temperature, dilute with ethyl acetate and filter through a short plug of celite with additional ethyl acetate. Wash the organics with water, dry over magnesium sulfate, filter and evaporate. Purification by flash column chromatography yields 2'-chlorobiphenyl-4-carboxylic acid methyl ester as a yellow solid. Dissolve the purified ester in tetrahydrofuran (0.25M) and add an equal volume of 1M sodium hydroxide. Stir vigorously at room temperature for 15 hours. Upon completion, acidify the reaction with conc. HCl and extract with ethyl acetate. Evaporation of the solvent yields 762 mg (67%) of the title compound. MS (m/e): 231.1 (M$^-$).

The following compounds are prepared essentially as described above.

| | |
|---|---|
| 6-(2-Chlorophenyl)pyridine-3-carboxylic acid | MS 233.9 (MH$^+$) |
| 6-(2,4-Difluorophenyl)pyridine-3-carboxylic acid | MS 235.9 (MH$^+$) |
| 6-Phenylpyridine-3-carboxylic acid methyl ester | MS 214.1 (MH$^+$) |
| 6-(2-Methylphenyl)pyridine-3-carboxylic acid | MS 214.0 (MH$^+$) |
| 2'-Trifluoromethylbiphenyl-4-carboxylic acid | MS 265.2 (M$^-$) |
| 2-Methylbiphenyl-4-carboxylic acid | MS 211.3 (M$^-$) |
| 3-Fluorobiphenyl-4-carboxylic acid | MS 215.1 (M$^-$) |
| 2',6'-Dichlorobiphenyl-4-carboxylic acid | MS 264.9 (M$^-$) |
| 2',6'-Difluorobiphenyl-4-carboxylic acid | MS 233.1 (M$^-$) |
| 2'-Methoxybiphenyl-4-carboxylic acid | MS 227.0 (M$^-$) |
| 3,4'-Difluorobiphenyl-4-carboxylic acid | MS 233.1 (M$^-$) |
| 3,2'-Difluorobiphenyl-4-carboxylic acid | MS 233.1 (M$^-$) |
| 3-Chlorobiphenyl-4-carboxylic acid | MS 231.1 (M$^-$) |
| 4-(Thien-2-yl)phenyl-1-carboxylic acid | MS 203.1 (M$^-$) |
| 4'-Fluorobiphenyl-4-carboxylic acid (Hydrolysis in dioxane at 60° C.) | MS 214.9 (M$^-$) |
| 3'-Fluorobiphenyl-4-carboxylic acid (Hydrolysis in dioxane) | MS 215.0 (M$^-$) |
| 3'-Cyanobiphenyl-4-carboxylic acid (Hydrolysis with LiOH in dioxane) | MS 222.0 (M$^-$) |

Method B

5-Phenylpyrazine-2-carboxylic acid

Combine 5-chloropyrazine-2-carboxylic acid methyl ester (626 mg, 3.64 mmol), phenylboronic acid (666 mg, 5.45 mmol), cesium fluoride (55 mg, 0.36 mmol) and Na$_2$CO$_3$ (964 mg, 9.09 mmol) in dimethylformamide (5 mL) and water (5 mL) with stirring. Place the heteroegeneous reaction mixture, open to the air, in an oil bath maintained at 80° C. After 5 minutes of heating, add Pd(OAc)$_2$ (81 mg 0.36 mmol) in one portion and stir until reaction turns black. Cool the reaction to room temperature, dilute with ethyl acetate, and filter through a short plug of celite with additional ethyl acetate. Wash the organics with water, dry over magnesium sulfate, filter and evaporate. Purification by flash column chromatography yields 2-phenylpyrimidine-5-carboxylic acid methyl ester as a yellow solid. Dissolve the purified ester in tetrahydrofuran (0.25M) and add an equal volume of 1M sodium hydroxide. Stir vigorously at room temperature for 15 hours. Upon completion, acidify the reaction with conc. HCl and extract with ethyl acetate. Evaporation of the solvent yields 63 mg (8%) of the title compound. $^1$H NMR (dimethylsulfoxide): 9.37 (s, 1H), 9.21 (s, 1H), 8.23-8.21 (m, 2H), 7.57-7.77 (m, 3H).

The following compounds are prepared essentially as described above.

| | |
|---|---|
| 2'-Fluoro-6'-trifluoromethylbiphenyl-4-carboxylic acid | MS 283.1 (M$^-$) |
| 3,2',4'-Trifluorobiphenyl-4-carboxylic acid | MS 251.1 (M$^-$) |
| 4'-Fluoro-2'-methoxybiphenyl-4-carboxylic acid | MS 245.1 (MH$^-$) |
| 3-Chloro-2',4'-difluorobiphenyl-4-carboxylic acid | MS 267.1 (M$^-$) |
| 4'-Fluoro-2'-methylbiphenyl-4-carboxylic acid | MS 229.0 (M$^-$) |
| 4'-Trifluoromethylbiphenyl-4-carboxylic acid | MS 265.1 (M$^-$) |
| 2-Fluoro-4-(thien-2-yl)phenyl-1-carboxylic acid | MS 221.1 (M$^-$) |

Method C

3',4'-Difluorobiphenyl-4-carboxylic acid

Combine 3,4-difluorobenzeneboronic acid (1.0 g, 5.2 mmol), methyl-4-bromobenzoate (0.241 g, 1.73 mmol), Pd(OAc)$_2$ (0.019 g, 0.086 mmol), tetrabutylammonium bromide (0.111 g, 0.345 mmol), and potassium phosphate (0.733 g, 3.454 mmol). Purge the reaction vessel with argon and add anhydrous dimethylformamide (20 mL) to the reaction mixture. Heat the sealed reaction vessel to 120° C. with stirring until completion. Cool the reaction to room temperature, dilute with ethyl acetate, and filter through a short plug of celite with additional ethyl acetate. Wash organics with water, dry over magnesium sulfate, filter, and evaporate. Purification by flash column chromatography yields 3',4'-difluorobiphenyl-4-carboxylic acid methyl ester as a yellow solid. Dissolve the purified ester in dioxane (45 mL) and add an equal volume of 1M aqueous sodium hydroxide. Heat the reaction vessel to 60° C. with stirring until completion. Remove the solvent by evaporation. Dissolve the residue in dichloromethane and wash with 1N aqueous hydrochloric acid. Dry the organics over magnesium sulfate, filter and evaporate to yield 0.048 g (12%) of the title compound. MS (m/e): 235 (M$^+$).

The following compounds are prepared essentially as described above.

| | |
|---|---|
| 6-(2-Fluorophenyl)pyridine-3-carboxylic acid | MS 218.0 (MH$^+$) |
| 3',5'-Dimethylbiphenyl-4-carboxylic acid | MS 225.0 (M$^-$) |
| 3',5'-Difluorobiphenyl-4-carboxylic acid | MS 233.0 (M$^-$) |
| 3',5'-Dichlorobiphenyl-4-carboxylic acid | MS 267.1 (M$^+$) |
| 3'-Chlorobiphenyl-4-carboxylic acid | MS 230.9 (M$^-$) |
| 2',3'-Difluorobiphenyl-4-carboxylic acid | MS 264.9 (M$^-$) |
| 4'-Chlorobiphenyl-4-carboxylic acid | MS 230.9 (M$^-$) |

Method D

2',4',6'-Trimethylbiphenyl-4-carboxylic acid

Combine 1-iodo-2,4,6-trimethylbenzene (2.966 g, 12.05 mmol), 4-carboxyphenylboronic acid (1.0 g, 6.026 mmol), Pd(OAc)$_2$ (0.0067 g, 0.005 mmol), tetrabutylammonium bromide (0.388 g, 1.2055 mmol), and potassium phosphate (2.557 g, 12.05 mmol). Purge the reaction vessel with argon and add anhydrous dimethylformamide (20 mL) to the reaction mixture. Heat the sealed reaction vessel to 120° C. with stirring until completion as determined by TLC. Cool reaction mixture to room temperature. Add methyl iodide (1.0 mL, 36.63 mmol) to reaction mixture with continued stirring until completion. Dilute the reaction with ethyl acetate and filter though a short plug of celite with additional ethyl acetate. Wash the organics with water, dry over magnesium sulfate, filter and evaporate. Purification by flash column chromatography yields 2',4',6'-trimethylbiphenyl-4-carboxylic acid methyl ester as a yellow solid. Dissolve the purified ester in dioxane (45 mL) and water (5 mL) containing 5 eq of LiOH with stirring at 60° C. Upon completion, evaporate the solvent, acidify the reaction mixture with hydrochloric acid, and extract with ethyl acetate. Dry the organics over magnesium sulfate, filter, and evaporate to yield 0.023 g (16%) of the title compound. MS (m/e): 239.1 (M$^-$).

The following compounds are prepared essentially as described above.

| | |
|---|---|
| 2',4',6'-Trifluorobiphenyl-4-carboxylic acid | MS 251.0 (M$^-$) |
| 2'-Fluoro-4'-Trifluoromethylbiphenyl-4-carboxylic acid | MS 283.0 (M$^-$) |

Method E

2',4'-Difluorobiphenyl-4-carboxylic acid

Combine 4-carbomethoxyphenylboronic acid (1.021 g, 5.67 mmol), 1-bromo-2,4-difluorobenzene (1.000 g, 5.181 mmol.), Pd(OAc)$_2$ (0.113 g, 0.50 mmol), triphenylphosphine (0.149 g, 0.505 mmol), and sodium carbonate (1.664 g, 0.568 mmol). Purge the reaction vessel with argon. Add dimethylformamide (20 mL) and water (2.0 mL) with stirring. Place sealed reaction in an 80° C. oil bath and allow to stir for 24 hours. Cool reaction to room temperature, dilute with ethyl acetate, and filter through a short plug of celite with additional ethyl acetate. Wash organics with water, dry over magnesium sulfate, filter, and evaporate. Purification by flash column chromatography yields 2',4'-difluorobiphenyl-4-carboxylic acid methyl ester as a yellow solid. Dissolve the purified ester in dioxane (5 mL) and add 5M sodium hydroxide (1 mL). Stir vigorously at 50° C. for 15 hours. Upon completion, acidify the reaction with conc. HCl and extract with ethyl acetate. Evaporation of the solvent yields 300 mg (24.7%) of the title compound. MS (m/e): 233.0 (M$^-$).

Method F

6-(2,6-Difluorophenyl)pyridine-3-carboxylic acid

Dissolve 6-chloropyridine-3-carboxylic acid methyl ester (6.86 g, 40 mmol) in toluene (100 mL) and heat to 90° C. Add phosphorous oxybromide (25 g, 87 mmol) in several portions and continue heating for 3 hours. Cool the reaction to room temperature and pour onto ice water. Extract the reaction with ethyl acetate and wash organics again with water then sodium hydrogencarbonate. Combine organics, dry over magnesium sulfate, filter, and evaporate to orange solid (8.1 g, 94%) which is an 8:1 mixture of 6-bromopyridine-3-carboxylic acid methyl ester:6-chloromopyridine-3-carboxylic acid methyl ester by $^1$H NMR.

Combine the mixture as obtained above (0.225 g, 1.04 mmol) with hexamethylditin (0.375 g, 1.15 mmol), Pd(OAc)$_2$ (21 mg, 0.09 mmol), and triphenylphosphine (25 mg, 0.09 mmol) in toluene (5 mL). Purge with N$_2$ and stir at 80° C. for 18 hours. Cool reaction to room temperature. Add a solution of 1-bromo-2,6-difluorobenzene (250 mg, 1.29 mmol) in toluene (1 mL) followed by Pd(OAc)$_2$ (21 mg, 0.09 mmol) and triphenylphosphine (25 mg, 0.09 mmol). Purge with N$_2$ and stir at 80° C. for an additional 18 hours. Cool reaction to room temperature. Evaporate the solvent and purify by column chromatography (silica, 10% ethyl acetate in hexane) to give 50 mg (20% yield) of 6-(2,6-difluorophenyl)pyridine-3-carboxylic acid ethyl ester. Hydrolyze the ester with 1 N sodium hydroxide solution (0.22 mL, 0.22 mmol) in methanol (3 mL) at room temperature for 3 days. Remove the volatiles under vacuum and combine the residue with 1 N hydrochloric acid solution. Collect the white solid by filtration, wash with water, and dry under vacuum to give 30 mg (63% yield) of the title compound. MS (m/e): 235.9 (MH$^+$).

Method G

3-Fluorobiphenyl-4-carboxylic acid

Combine methyl 2-fluoro-4-bromobenzoate (1.25 g, 5.36 mmol), phenylboronic acid (1.30 g, 10.72 mmol) and CsF (2.02 g, 13.40 mmol) in dimethylformamide (25 mL) and water (3.0 mL) with stirring. Place the hetereogeneous reaction mixture open to the air in an oil bath maintained at 80° C. After 5 minutes of heating, add Pd(OAc)$_2$ (120 mg, 0.536 mmol) in one portion and stir until reaction turns black. Cool reaction to room temperature, dilute with ethyl acetate and filter through a short plug of celite with additional ethyl acetate. Wash organics with water, dry over magnesium sulfate, filter and evaporate. Purification by flash column chromatography yields 3-fluorobiphenyl-4-carboxylic acid methyl ester as a solid. Dissolve the purified ester in tetrahydrofuran (0.25M) and add an equal volume of 1M sodium hydroxide. Stir vigorously at room temperature for 15 hours. Upon completion, acidify the reaction with conc. HCl and extract with ethyl acetate. Evaporation of the solvent yields 965 mg (84%) of the title compound. MS (m/e): 214.9 (M⁻).

The following compounds are prepared essentially as described above.

| | |
|---|---|
| 3-Fluoro-2'-methylbiphenyl-4-carboxylic acid | MS 229.0 (M⁻) |
| 2'-Chloro-3-fluorobiphenyl-4-carboxylic acid | MS 205.1 (M⁻) |
| 3-Fluoro-2'-trifluoromethylbiphenyl-4-carboxylic acid | MS 283.1 (M⁻) |

Method H

2-Fluoro-6-phenylpyridine-3-carboxylic acid

Dissolve 2,6-difluoropyridine (5.0 mL, 5.51 mmol) in anhydrous tetrahydrofuran (30 mL) and cool to −40° C. Add a solution of phenyl lithium (1.8 M hexanes, 30.6 mL) dropwise over 5 minutes. Stir the resulting purple reaction at −40° C. for 30 minutes and bring to room temperature. Quench the reaction with water and extract the solution with ethyl acetate several times. Combine the organic extracts, dry over magnesium sulfate, filter and evaporate onto silica gel. Purification by flash column chromatography yields 2-fluoro-6-phenylpyridine 1.0 g (12%) as a yellow oil.

Cool a solution of LDA (3.46 mmol) in anhydrous tetrahydrofuran (6 mL) to −78° C. Cannulate the 2-fluoro-6-phenylpyridine in anhydrous tetrahydrofuran (6 mL) to the cooled LDA solution. Stir at −78° C. for 30 minutes then bubble carbon dioxide gas through the solution for 10 minutes. Allow the reaction to come to room temperature and purge with argon. Extract the reaction with 1M sodium hydroxide and discard the organics. Acidify the aqueous layer with conc. HCl and extract with ethyl acetate. Dry the organic layer over magnesium sulfate, filter and evaporate to yield the title compound as a light yellow solid (405 mg, 65%). MS (m/e): 216.1 (M⁻).

Method J

3,5-Difluorobiphenyl-4-carboxylic acid

Combine 1-bromo-3,5-difluorobenzene (0.863 mL, 7.50 mmol) and phenylboronic acid (1.22 g, 10.00 mmol) and subject to conditions described in Method G to yield 1.3 g of 3,5-difluorobiphenyl.

Dissolve crude 3,5-difluorobiphenyl (1.3 g, 6.83 mmol) in tetrahydrofuran (14 mL) and cool to −78° C. Prepare LiTMP from the addition of BuLi (1.6 M soln in hexanes, 5.33 mL) to tetramethyl piperidine (1.4 mL, 1.25 equiv) at −78° C. in tetrahydrofuran (14 mL). Cannulate the cooled LiTMP into the cooled 3,5-difluorobiphenyl and stir the reaction at −78° C. for 1 hour. Bubble carbon dioxide gas through the solution for 5 minutes, warm the reaction to room temperature, pour into 50 mL of 1M sodium hydroxide, and extract with 50 mL ethyl acetate. Discard the organic layer. Acidify the remaining aqueous layer with conc. HCl and extract twice with ethyl acetate. Dry the organics over magnesium sulfate, filtered, and evaporate to give 1.22 g of the title compound as a white solid (77%). MS (m/e): 233.1 (M⁻).

Method K

3,2',6'-Trifluorobiphenyl-4-carboxylic acid

Combine methyl 4-bromo-2-fluorobenzoate (3.66 g, 15.75 mmol), 4,4,5,5,4',4',5',5'-octamethyl-2,2'-bi-1,3,2-dioxaborolanyl (5.0 g, 19.68 mmol) and potassium acetate (4.63 g, 47.19 mmol) in dimethylsulfoxide (40 mL) and purge the solution with argon. Add PdCl$_2$(1,1'-bis(diphenylphosphino)ferrocene)$_2$ (10 mol %, 1.35 g) and purge the solution with argon again. Heat the reaction to 80° C. for 3 hours and cool to room temperature. Wash the reaction with water and extract with ethyl acetate and concentrate. The resulting black oil is re-dissolved in 1:2 ethyl acetate: hexanes, filtered through a short plug of silica gel, and concentrated. 2-Fluoro-4-(4,4,5,5-tetramethyl-1,3,2-dioxaborolan-2-yl)benzoic acid methyl ester is obtained as a yellow oil.

Dissolve the resulting yellow oil in acetone (100 mL) and combine with NaIO$_4$ (10.1 g, 47.25 mmol), NH$_4$OAc (3.63 g, 47.25 mmol), and water (50 mL) at room temperature. Stir at room temperature for 18 hours, transfer to a separatory funnel and extract with ethyl acetate several times. Dry the combined organics over magnesium sulfate, filter and concentrate to yield 3.0 g of 3-fluoro-4-carbomethoxybenzene boronic acid as an off-white solid.

The boronic acid obtained above (800 mg, 4.04 mmol) and 2,6-difluorobromobenzene (1.17 g, 6.06 mmol) are coupled according to the procedure described in Method G to give 380 mg of the title compound. MS (m/e): 251.1 (M⁻).

Method L

6-Phenylpyridazine-3-carboxylic acid

6-Phenylpyridazin-3-ol (5.0 g, 29.06 mmol) is dissolved in toluene (100 mL) and heated to 90° C. Phosphorous oxybromide (25 g, 87.19 mmol) is added in several portions and the reaction is heated for 30 minutes. The resulting yellow solution is cooled to room temperature, poured onto ice water, and extracted with ethyl acetate. The organic layers are further washed with water and 1M sodium hydroxide, dried over magnesium sulfate, filtered, and evaporated to a yellow solid. Recrystallization from CHCl$_3$ gives 2.17 g of 3-bromo-6-phenylpyridazine.

3-Bromo-6-phenylpyridazine (1.0 g, 4.25 mmol) is combined with dimethylformamide (5 mL), MeOH (5 mL), triethylamine (1.18 mL, 8.50 mmol), and Pd(OAc)$_2$ (76 mg, 0.33 mmol) and the mixture evacuated. 1,1'-Bis(diphenylphosphino)ferrocene (235 mg, 0.42 mmol) is added and the reaction is again evacuated. Carbon dioxide gas is bubbled through the solution for 5 minutes, and the reaction is placed under 50 psi (345 kPa) of carbon dioxide. The resulting solution is heated at 50° C. for 18 hours. Cool the reaction to room temperature, dilute with water, and extract with ethyl acetate. Dry the organics over magnesium sulfate, filter, and evaporate onto silica gel and subjected to flash column chromatography.

Hydrolysis using conditions outlined in Method A gives 80 mg of the title compound. $^1$H NMR (CDCl$_3$): 8.24 (d, 1H, J=8.8 Hz), 8.18-8.15 (m, 2H), 8.0 (d, 1H, J=9.2 Hz), 7.56-7.55 (m, 3H).

Method M 6-(4-Fluorophenyl)pyridine-3-carboxylic acid

Combine 6-bromopyridine-3-carboxylic acid methyl ester (1.03 g, 4.78 mmol), 4-fluorophenylboronic acid (1.88 g, 13.41 mmol), and cesium fluoride (2.55 g, 16.78 mmol) in dimethylformamide (25 mL) and water (4 mL) with stirring. Place the hetereogeneous reaction mixture, open to the air, in an oil bath maintained at 80° C. After 5 minutes of heating, add Pd(OAc)$_2$ (150 mg, 0.67 mmol) in one portion. After 17 hours, cool the reaction to room temperature, dilute with ethyl acetate and filter through a short plug of celite with additional ethyl acetate. Wash the organics with water, dry over magnesium sulfate, filter and evaporate. Purification by flash column chromatography yields 6-(4-fluorophenyl)pyridine-3-carboxylic acid methyl ester as a yellow solid. Dissolve the purified ester in tetrahydrofuran (0.25M) and add an equal volume of 1M sodium hydroxide. Stir vigorously at room temperature for 15 hours. Upon completion, acidify the reaction with conc. HCl and collect the white precipitate by filtration. Drying under vacuum yields 385 mg (37%) of the title compound. MS (m/e): 218.1 (MH$^+$)

The following compound is prepare essentially as described above.

| | |
|---|---|
| 6-(Thien-2-yl)pyridine-3-carboxylic acid | MS 205.9 (MH$^+$) |

Method N 6-(4-Fluoro-2-methylphenyl)pyridine-3-carboxylic acid

Combine 6-bromopyridine-3-carboxylic acid methyl ester (387 mg, 1.79 mmol), 4-fluoro-2-methylphenylboronic acid (338 mg, 2.19 mmol), Pd(OAc)$_2$ (40 mg, 0.18 mmol), cesium fluoride (27 mg, 0.18 mmol) and sodium carbonate (570 mg, 5.38 mmol) in dimethylformamide (6 mL) and water (6 mL) with stirring. Purge the reaction mixture with N$_2$, add triphenylphosphine (47 mg, 0.18 mmol), and purge again with N$_2$. Place the sealed reaction in an oil bath maintained at 80° C. and allow to stir for 17 hours. Cool the reaction to room temperature and pass through a short plug of silica gel. Wash the column with dichloromethane (100 mL) followed by aqueous methanol (100 mL, 3 methanol/1 water). Reduce the combined fractions in vacuo and suspend the residual solid in water (10 mL). Filter to remove a black solid and acidify with 1N hydrochloric acid solution to pH 4. A white precipitate forms which is collected by filtration and dried to give 306 mg (74%) of the title compound. MS (m/e): 231.9 (MH$^+$).

The following compounds are prepared essentially as described above.

| | |
|---|---|
| 6-(2,4-Difluorophenyl)pyridine-3-carboxylic acid | MS 236.0 (MH$^+$) |
| 6-(2-Fluorophenyl)pyridine-3-carboxylic acid | MS 218.0 (MH$^+$) |
| 2'-Fluorobiphenyl-4-carboxylic acid | MS 215.1 (M$^-$) |
| 2'-Methylbiphenyl-4-carboxylic acid | MS 211.2 (M$^-$) |

PREPARATION 1-1

2-(6-Fluoropyridin-2-ylsulfanyl)ethylamine

Suspend sodium hydride (138 mg, 5.46 mmol) in tetrahydrofuran (6 mL) and cool to 0° C. in an ice bath. Add (2-mercaptoethyl)carbamic acid tert-butyl ester (0.461 mL, 2.73 mmol) dropwise over 5 minutes. Stir reaction for 30 minutes, add 2,6-difluoropyridine (0.495 mL, 0.546 mmol), remove ice bath and stir an additional hour. Re-cool reaction and quench with water. Extract with 1/1 hexanes/ethyl acetate. Dry organics over magnesium sulfate, filter and evaporate. Perform flash column chromatography (ethyl acetate/hexanes). Dissolve resulting orange oil in trifluoroacetic acid (3 mL) and stir for 15 minutes. Concentrate the reaction with a stream of dry nitrogen, re-dissolve in dry methylene chloride and evaporate to give 120 mg of the title compound as an orange oil. $^1$H NMR (d MeOH): 7.70 (m, 1H), 7.22 (m, 1H), 6.78 (m, 1H), 3.44 (m, 2H), 3.34 (m, 2H).

PREPARATION 2-1

2-(5-Phenylfuran-2-yl)ethylamine

Combine 5-phenylfuran-2-carbaldehyde (808 mg, 4.69 mmol), methanol (2.0 mL), and nitromethane (1.13 mL) and cool. Add a combination of 0.20 mL of 1M sodium hydroxide and 0.70 mL of water to the reaction. Stir the reaction for 15 minutes, dilute with water (5 mL), add 1.0 mL of concentrated hydrochloric acid, and stir for 20 additional hours. Extract the reaction with ethyl acetate, dry organics, filter and evaporate to yield 1.14 g of 2-(2-nitrovinyl)-5-phenylfuran as a brown oil which can be used without further purification. MH+ 216.0

Cool lithium aluminum hydride (21 mL, 1.0 M solution in ether) to 0° C. and add 2-(2-nitrovinyl)-5-phenylfuran (760 mg, 3.53 mmol in 5 mL of ether). Stir reaction to room temperature for 15 hours. Re-cool reaction to 0° C. and quench with 0.80 mL of water, followed by 0.80 mL 1M sodium hydroxide and 0.80 mL of water (×3). Dilute reaction with additional tetrahydrofuran and stir at room temperature for 2 hours. Filter and dry over sodium sulfate and filter again. Concentrate and perform flash column chromatography (methylene chloride, MeOH, NH$_4$OH) to give 134 mg (20% yield) of the title compound as a brown oil. MH+ 188.0.

PREPARATION 3-1

2-(4-Phenylpyrazol-1-yl)ethylamine

Dissolve 4-phenylimidazole (1.0075 g, 6.99 mmol) in 10 mL tetrahydrofuran and add it dropwise to a suspension of sodium hydride (60%) (366.4 mg, 9.16 mmol) in 10 mL tetrahydrofuran. After 1.5 hours, heat the reaction to reflux and allow it to stir for 2 hours. Cool the reaction to room temperature and quench the reaction by adding a solution of N-(2-bromomethyl)phthalimide (1.8649 g, 7.34 mmol)

dropwise in 10 mL tetrahydrofuran. Heat the reaction to reflux and allow to stir for an additional 18 hours. Add water to the reaction and remove tetrahydrofuran in vacuo. Partition the residue between ethyl acetate and brine. Dry the organic layer with magnesium sulfate. Filter and remove the solvent in vacuo to afford 2.0513 g of crude material. Perform silica gel chromatography (2% MeOH/CHCl$_3$) to obtain 182.4 mg of 2-(2-(4-phenyl-imidazol-1-yl)-ethyl)-isoindole-1,3-dione (8%). MS (m/e): 318.0 (M+1).

Dissolve this material (182.4 mg, 0.575 mmol) in 10 mL absolute ethanol. Add hydrazine hydrate (575.7 mg, 11.5 mmol) to the reaction mixture and heat the reaction to reflux. After 4 hours, cool the reaction. Filter the reaction mixture and concentrate the filtrate in vacuo. Partition the residue between methylene chloride and water. Extract the aqueous layer with methylene chloride (2×). Dry the organic layer with magnesium sulfate. Filter and remove the solvent in vacuo to afford 59.3 mg of the title compound (55% yield). MS (m/e): 188.0 (M+1).

PREPARATION 4-1

C-(5-Phenyl-[1,3,4]oxadiazol-2-yl)methylamine

Dissolve benzoyl chloride (6.82 g, 48.51 mmol) in 20 mL dioxane and add it dropwise to a refluxing mixture of oxamic hydrazide (5.00 g, 48.51 mmol) and sodium hydrogencarbonate (4.08 g, 48.67 mmol) in 200 mL dioxane. Allow the reaction to stir at reflux for 4 hours and filter it hot. Concentrate the filtrate in vacuo to afford 9.89 g of a white solid. Recrystallize this solid from water to afford 4.4058 g of 2-(N'-benzoyl-hydrazino)-2-oxo-acetamide. MS (m/e): 206.1 (M−1). Suspend this material (1.1113 g, 5.36 mmol) in 25 mL of POCl$_3$ and heat the reaction mixture to 100° C. for 3 hours. Cool the reaction to room temperature and remove the solvent in vacuo. Dissolve the residue in ethyl acetate and add it slowly to an ice-cold solution to saturated aqueous sodium hydrogencarbonate. Dry the organic layer with magnesium sulfate. Filter and remove the solvent in vacuo to afford 574.7 mg of crude material. Perform silica gel chromatography (100% CHCl$_3$) to obtain 241.0 mg of 5-phenyl-[1,3,4]oxadiazole-2-carbonitrile (26%). MS (m/e): 171(M). Reduce this material (104.8 mg, 0.612 mmol) by dissolving it in a mixture of 10 mL absolute ethanol/1 mL concentrated HCl/51.5 mg Pd (black) and exposing it to 1 atm of H$_2$ for 2.5 hours. Filter the reaction over a pad of celite and concentrate the filtrate in vacuo. Partition the residue between methylene chloride and water. Separate and basify the aqueous layer with 5 N sodium hydroxide and extract the aqueous layer with methylene chloride (3×). Dry the combined organic phase with magnesium sulfate. Filter and remove the solvent in vacuo to afford 28.2 mg of the titled product (26% yield). MS (m/e): 176.0 (M+1).

PREPARATION 5-1

2-(2-Phenylimidazol-1-yl)ethylamine

Dissolve 2-phenylimidazole (1.0892 g, 7.55 mmol) in 10 mL dimethylformamide and add it dropwise to a suspension of NaH (60%) (400.5 mg, 10.01 mmol) in 10 mL dimethylformamide. After 1 hour, heat the reaction to 70° C. and allow it to stir for 2 hours. Add a solution of N-(2-bromomethyl)phthalimide (1.8649 g, 7.34 mmol) dropwise in 5 mL dimethylformamide. Allow the reaction to stir for an additional 48 hours. Quench the reaction with water and concentrate in vacuo. Dissolve the residue in ethyl acetate and wash it with brine (3×). Dry the organic layer with magnesium sulfate. Filter and remove the solvent in vacuo to afford 2.1776 g of crude material. Perform silica gel chromatography (1% MeOH/CHCl$_3$) to obtain 90.1 mg of 2-(2-(2-phenylimidazol-1-yl)ethyl)isoindole-1,3-dione. MS (m/e): 318.0 (M+1).

Dissolve this material (90.1 mg, 0.284 mmol) in 10 mL absolute ethanol. Add hydrazine hydrate (284.3 mg, 5.68 mmol) to the reaction mixture and heat the reaction to reflux. After 17 hours, cool the reaction. Filter the reaction mixture and concentrate the filtrate in vacuo. Partition the residue between methylene chloride and water. Extract the aqueous layer with methylene chloride (2×). Dry the organic layer with magnesium sulfate. Filter and remove the solvent in vacuo to afford 59.3 mg of the titled product (24%). MS (m/e): 188.0 (M+1).

PREPARATION 6-1

(2-(4-Fluorophenylsulfanyl)ethyl methylamine

Reflux a mixture of (2-bromoethyl)methylamine hydrobromic acid salt (500 mg, 2.28 mmol), 4-fluorobenzenethiol (0.243 mL, 2.28 mmol), and potassium t-butoxide (512 mg, 4.56 mmol) in acetonitrile (10 mL) for 17 hours. Remove the solvent under vacuum and dissolve the residue in ether and 5 N sodium hydroxide solution. Extract the organic layer with 1 N hydrochloric acid solution. Neutralize the acidic aqueous layer with 5 N sodium hydroxide solution and extract twice with ether. Dry the combined ether extracts over magnesium sulfate and reduce under vacuum to give 260 mg of the titled compound as an oil.

PREPARATIONS 6-2 AND 6-3 ARE PREPARED ESSENTIALLY AS 6-1

| Prep # | Compound Name |
|---|---|
| 6-2 | Methyl(2-phenylsulfanylethyl)amine |
| 6-3 | 2-Phenylsulfanylethylamine |

PREPARATION 7-1

2-(5-Methylthiophen-2-yl)ethylamine

A. 2-(3-tert-Butoxy-propyl)-isoindole-1,3-dione

Dissolve 2-(3-hydroxypropyl)isoindole-1,3-dione (2 g, 9.74 mmol, 1 eq) in 40 mL of dichloromethane under N$_2$. Add sulfuric acid (780 μL) and cool reaction mixture to −5° C. Condense isobutylene gas to a liquid using a −78° C. cold finger charged with dry ice and acetone. Add approximately 20 mL of the condensed liquid to the reaction mixture and slowly warm the solution to room temperature overnight while stirring. Add saturated, aqueous sodium hydrogencarbonate to the reaction mixture and extract product into the organics. Wash separated organic layer with water and dry over magnesium sulfate to give 1.969 g (77% yield) of 2-(3-tert-butoxypropyl)isoindole-1,3-dione as a colorless oil.

B. 3-tert-Butoxypropylamine

Add 100 mL of ethanol to 2-(3-tert-butoxypropyl)isoindole-1,3-dione (1.969 g, 7.535 mmol, 1 eq) under $N_2$. Add hydrazine (2.4 g, 75.35 mmol, 10 eq) to the reaction mixture and heat to 60° C. overnight. Cool reaction to 0° C. and filter off solid phthalhydrazide byproduct. Remove solvent from the eluent on the rotovap to give 580 mg of a crude mixture of both phthalhydrazide and desired product (approximately 122 mg, 12% yield) 3-tert-butoxypropylamine. MS (m/e): 132.1 (MH+)

C. 2-Methyl-5-(2-nitrovinyl)thiophene

Cool a solution of 5-methylthiophene-2-carbaldehyde (1 g, 7.9 mmol, 1 eq) and nitromethane (484 mg, 7.9 mmol, 1 eq) in methanol (3 mL) to 10° C. Add sodium hydroxide (332 mg, 8.3 mmol, 1.05 eq) as an aqueous solution (1.5 mL) to the reaction mixture. Stir reaction for 15 minutes and add ice water. Add this mixture to an aqueous HCl solution (1.67 mL concentrated HCl in 2.4 mL water) and stir overnight. Extract product with ethyl acetate, separate organics, dry with magnesium sulfate, and concentrate on rotovap to give 2-methyl-5-(2-nitrovinyl)thiophene (966 mg, 72% yield) as a crude solid.

D. 2-(5-Methyl-thiophen-2-yl)-ethylamine

Add 2-methyl-5-(2-nitrovinyl)thiophene (483 mg crude, 2.855 mmol, 1 eq) as a solution in diethyl ether (15 mL) to a solution of lithium aluminum hydride (227 mg, 5.995 mmol, 2.1 eq) in diethyl ether (5.995 mL) at a rate such as to maintain gentle reflux of the solution. Stir reaction for 5 minutes. Cautiously add water followed by several small portions of potassium sodium tartrate. Stir reaction vigorously for 1 hour and then let stand overnight. Separate organics, dry with magnesium sulfate, and concentrate on rotovap to give 360 mg of crude product as an oil. Perform column chromatography to give 82 mg (20% yield) of 2-(5-methylthiophen-2-yl)ethylamine. MS (m/e): 142.0 (MH+).

PREPARATION 8-1

C-(5-Bromofuran-2-yl)methylamine

Prepare the title compound according to the procedure found in Tetrahedron Letters, 40(12), pg. 2295-2299 (1999).

PREPARATION 9-1

C-(5-Ethylfuran-2-yl)methylamine

Prepare the title compound according to the procedure found in Tetrahedron Letters 40(12), pg. 2295-2299 (1999).

PREPARATION 10-1

3-Pyridin-2-yl-propylamine

A. 2-(3-Pyridin-2-yl-propyl)isoindole-1,3-dione

Cool a mixture of phthalimide (0.54 g, 3.7 mmol) and $PPh_3$ (0.95 g, 3.6 mmol) in tetrahydrofuran (5.0 mL) to 0° C. Add a solution of 2-pyridine propanol (0.50 g, 3.7 mmol) and diethyl azodicarboxylate (0.60 mL, 3.8 mmol) in tetrahydrofuran (5.0 mL) dropwise over 4 minutes. After 4 hours, concentrate the reaction mixture, redissolve in diethyl ether (50 mL) and filter. Concentrate the filtrate. Perform flash chromatography on silica gel eluting with 20% of a 80:18:2 $CHCl_3$/MeOH/concentrated $NH_4OH$ solution in methylene chloride to afford 2-(3-pyridin-2-yl-propyl)isoindole-1,3-dione as a red oil which is used without further purification.

$^1$H NMR ($CDCl_3$) δ 8.45-8.50 (m, 1H), 7.37-7.88 (m, 5H), 6.99-7.16 (m, 2H), 3.75-3.81 (m, 2H), 2.85-2.90 (m, 2H), 2.20-2.25 (m, 2H).

B. 3-Pyridin-2-yl-propylamine

Place 2-(3-pyridin-2-yl-propyl)isoindole-1,3-dione (7.0 g, 26.0 mmol) in a flask and add a solution of hydrazine (4.0 mL) in MeOH (200 mL). After 12 hours, filter the mixture and concentrate the filtrate, titrate with methylene chloride, and filter a second time. Perform flash chromatography on silica gel eluting with 80:18:2 $CHCl_3$/MeOH/concentrated $NH_4OH$ to afford the title compound as a brown oil (4.59 g) MS: m/e=137 (MH$^+$).

PREPARATION 11-1

3-Pyridin-3-yl-propylamine

A. 2-(3-Pyridin-3-yl-propyl)isoindole-1,3-dione

Cool a mixture of phthalimide (5.4 g, 37 mmol) and $PPh_3$ (9.6 g, 37 mmol) in tetrahydrofuran (80 mL) to 0° C. Add dropwise a solution of 3-pyridine propanol (5.0 g, 37 mmol) and diethyl azodicarboxylate (5.8 mL, 37 mmol) in tetrahydrofuran (50 mL). After 2 hours, dilute the reaction mixture with methylene chloride (100 mL), and water (100 mL). Wash the organic layer with water (100 mL), then brine (100 mL). Dry over magnesium sulfate, filter and concentrate to afford 2-(3-pyridin-3-yl-propyl)isoindole-1,3-dione as a yellow solid which can be used without further purification.

$^1$H NMR ($CDCl_3$) δ 7.14-8.47 (m, 8H), 3.75-3.79 (m, 2H), 2.67-2.72 (m, 2H), 2.04-2.09 (m, 2H).

B. 3-Pyridin-3-yl-propylamine

Add a solution of hydrazine (4.0 mL) in methanol (200 mL) to 2-(3-pyridin-3-yl-propyl)isoindole-1,3-dione (8.0 g, 30 mmol). After 48 hours, filter the mixture and concentrate the filtrate. Triturate in methylene chloride (100 mL) and filter a second time. Perform flash-chromatography on silica gel eluting with 80:18:2 $CHCl_3$/MeOH/concentrated $NH_4OH$ to afford the title compound as a yellow oil (3.3 g,). MS m/e=137 (MH$^+$).

PREPARATION 12-1

3-Pyridin-4-yl-propylamine

A. 2-(3-Pyridin-4-yl-propyl)isoindole-1,3-dione

Cool a mixture of phthalimide (5.4 g, 37 mmol) and $PPh_3$ (9.6 g, 37 mmol) in tetrahydrofuran (80 mL) to 0° C. Add dropwise a solution of 4-pyridine propanol (5.0 g, 37 mmol) and diethyl azodicarboxylate (5.8 mL, 37 mmol) in tetrahydrofuran (55 mL). After 2 hours warming to room temperature, concentrate the reaction mixture to a brown paste and perform flash-chromatography on silica gel eluting with 20% of a 80:18:2 $CHCl_3$/MeOH/concentrated $NH_4OH$) solution in methylene chloride to afford 2-(3-pyridin-4-ylpropyl)isoindole-1,3-dione as a yellow solid. TLC (SiO$_2$): R$_f$=0.68 [20% of a 80:18:2 CHCl$_3$/MeOH/concentrated NH$_4$OH solution in methylene chloride].

B. 3-Pyridin-4-yl-propylamine

Add a solution of hydrazine (4.0 mL) in methanol (200 mL) to 2-(3-pyridin-4-yl-propyl)isoindole-1,3-dione (8.0 g, 30 mmol). After 48 hours, filter the mixture and concentrate the filtrate, triturate with methylene chloride (150 mL), and filter a second time. Perform the filtrate via flash chromatography on silica gel eluting with 80:18:2 CHCl$_3$/MeOH/ concentrated NH$_4$OH) to afford the title compound as a yellow oil (3.42 g). MS: m/e=137 (MH$^+$).

PREPARATION 13-1

2-Phenoxyethylamine

Add sodium hydride (60% in mineral oil, 6.63 g, 166 mmol) to a solution of 2-hydroxyethylamine (10.0 mL, 166 mmol) in dioxane (150 mL), at room temperature under nitrogen. Stir for 10 minutes at room temperature. Add 2-chloropyridine (15.6 mL, 166 mmol) and heat the reaction mixture to reflux. After stirring at reflux for 14 hours, cool the reaction mixture to room temperature and dilute with water (100 mL), and methylene chloride (200 mL). Extract the aqueous layer with methylene chloride (2×100 mL). Combine the organic layers with brine (200 mL), dry (magnesium sulfate), filter and concentrate to an orange oil. Perform flash chromatography on silica gel eluting with 50% of a 80:18:2 CHCl$_3$/MeOH/concentrated NH$_4$OH) solution in methylene chloride to afford the title compound as a yellow oil (17.9 g). MS: m/z=139 (MH$^+$).

PREPARATION 14-1

2-Phenylsulfanyl-ethylamine

Mix 2-aminoethanethiol hydrochloride (4.07 g, 35.6 mmol) in dioxane (75 mL) at 50° C. Add sodium hydride (60% in mineral oil, 2.84 g, 71.0 mmol) at room temperature under nitrogen. Stir the reaction for 5 minutes. Add 2-chloropyridine (3.5 mL, 37 mmol) to the mixture. Reflux the mixture for 24 hours, and then cool to room temperature. Add water (100 mL), and methylene chloride (300 mL) to this mixture. Extract the aqueous layer with methylene chloride (3×50 mL). Wash the combined organic phase with brine (200 mL), dry (magnesium sulfate), filter and concentrate to an orange oil. Perform flash chromatography on silica gel eluting with 50% (80:18:12 CHCl$_3$/MeOH/concentrated NH$_4$OH)/methylene chloride to afford the title compound as a yellow oil (1.67 g) m/e=155 (MH$^+$).

PREPARATION 15-1

C-(2-Methylthiazol-5-yl)methylamine

A. 5-Bromomethyl-2-methylthiazole

To a solution of 2,5-dimethylthiazole (0.730 g, 5.10 mmol) in benzene (80 mL). add N-bromosuccinimide (0.908 g, 5.10 mmol) and a catalytic amount of benzoyl peroxide. Heat the solution at reflux for 2 hours and stir overnight at room temperature. Cool the mixture, dilute with diethyl ether, wash with saturated Na$_2$SO$_3$ (75 mL), followed by saturated sodium hydrogencarbonate (75 mL), dry (Na$_2$SO$_4$), filter, and concentrate. Perform flash chromatography on silica gel eluting with 100% diethyl ether to afford 390 mg of the title compound.
$^1$H NMR (CDCl$_3$) δ7.39 (s, 1H), 4.70 (s, 2H), 2.48 (s, 3H).

B.
2-(2-Methylthiazol-5-ylmethyl)isoindole-1,3-dione

Add 5-bromomethyl-2-methylthiazole (390 mg, 2.03 mmol) in dimethylformamide (2 mL) dropwise to a suspension of potassium phthalimide (434 mg, 2.34 mmol) in dimethylformamide (8 mL). Stir the reaction under nitrogen at room temperature overnight. Concentrate the mixture in vacuo, dissolve in ethyl acetate (100 mL), and wash with water (100 mL). Dry the organic phase (sodium sulfate), filter, and concentrate. Perform flash chromatography on silica gel, eluting first with 4:1 hexane/ethyl acetate, then 100% ethyl acetate to afford 210 mg of 2-(2-methylthiazol-5-ylmethyl)isoindole-1,3-dione as a tan solid. MS: m/z=259 (MH$^+$).

C. C-(2-Methylthiazol-5-yl)methylamine

Suspend 2-(2-methylthiazol-5-ylmethyl)isoindole-1,3-dione (210 mg, 0.814 mmol) in 6N HCl (8 mL) and heat at reflux for 2.5 hours. Cool to room temperature and stir for an additional 5 hours. Basify the mixture with 2 N sodium hydroxide, extract with methylene chloride (3×50 μL), dry (sodium sulfate), filter, and concentrate to afford 70 mg (61% yield) of the title compound as a brown oil. $^1$H NMR (CDCl$_3$) δ 7.34 (s, 1H), 4.11 (s, 2H), 2.45 (s, 3H), 1.70 (br s, 2H).

PREPARATION 16-1

2-Thiazol-2-yl-ethylamine

A. 3-Thiazol-2-yl-acrylic acid

Mix 2-formyl thiazole (10.0 g, 88.4 mmol) and malonic acid (9.2 g, 88.4 mmol). Dissolve in pyridine (7.2 mL, 88.5 g) and add 3 drops of piperidine. Heat the mixture at 100° C. under nitrogen for 3 hours, cool, dilute with water, and filter the solids to afford 1.7 g of the title compound as a white solid. Concentrate the filtrate, acidify with 1N HCl, extract with ethyl acetate (2×100 mL), wash with brine (100 mL), dry (sodium sulfate), filter and concentrate to afford an additional 4.8 g of 3-thiazol-2-yl-acrylic acid MS: m/e=156 (MH$^+$).

B. 3-Thiazol-2-yl-propionic acid

Mix and suspend 3-thiazol-2-yl-acrylic acid (580 mg, 3.74 mmol) and 5% Pd/C (270 mg) in ethanol (200 mL). Purge the mixture with nitrogen. Then purge with hydrogen for 30 minutes and stir under 1 atmosphere of hydrogen for 6 hours. Filter the reaction mixture through Celite® and wash the filter cake with additional ethanol. Concentrate the filtrate to afford 550 mg (94%) of 3-thiazol-2-yl-propionic acid as a white solid. MS: m/e=158 (MH$^+$).

C. (2-Thiazol-2-yl-ethyl)carbamic acid 2-trimethylsilanyl-ethyl ester

Suspend 3-thiazol-2-yl-propionic acid (650 mg, 4.14 mmol) in toluene (20 mL) under nitrogen. Add triethylamine (580 μL, 4.14 mmol) followed by diphenyl phosphoryl azide (1.14 g, 4.14 mmol). Heat the reaction mixture at 80° C. for 2 hours then add trimethylsilyl ethanol (1.2 mL, 8.28 mmol) and heat the solution an additional hour at 80° C. Cool to 30° C. overnight. Concentrate the mixture, basify with 10% sodium hydroxide, and extract with ethyl acetate (2×100 mL). Wash the organic phase with brine (100 mL), dry over sodium sulfate, filter, and concentrate. Perform flash chromatography on silica gel eluting with 1:1 hexane/ethyl acetate to afford 570 mg of (2-thiazol-2-yl-ethyl)carbamic acid 2-trimethylsilanyl-ethyl ester as a yellow oil. $^1$H NMR (CDCl$_3$) δ 7.71 (d, J=3 Hz, 1H), 7.23 (d, J=3 Hz, 1H), 5.30 (br s, 1H), 4.02-4.21 (m, 2H), 3.58-3.70 (m, 2H), 3.19-3.29 (m, 2H), 0.95-1.06 (m, 2H), 0.05 (s, 9H).

D. 2-Thiazol-2-yl-ethylamine

Dissolve (2-thiazol-2-yl-ethyl)carbamic acid 2-trimethylsilanyl-ethyl ester (570 mg, 2.1 mmol) in 1M TBAF in tetrahydrofuran (2.5 mL) and heat the solution under nitrogen for 1 hour at 50° C. Then add an additional 2.1 mL of 1M TBAF solution. After 1 hour, add 2.5 mL additional 1M TBAF and cool the mixture to room temperature and stir overnight. Concentrate the mixture and chromatograph with 93:7:1 CHCl$_3$/MeOH/concentrated NH$_4$OH. Dilute the resulting impure material with water, extract with ethyl acetate (2×50 mL), and the wash the organic phase with brine (50 mL), dry (Na$_2$SO$_4$), filter, and concentrate to afford 60 mg of the title compound. Extract the aqueous layer with CHCl$_3$ (7×100 mL) to afford an additional 290 mg of the title compound. Combine the lots and rechromatograph with 93:7:1 CHCl$_3$/MeOH/concentrated NH$_4$OH to afford 160 mg of the title compound. MS: m/e=129 (MH$^+$)

PREPARATION 17-1

C-(2-Phenyl-oxazol-5-ylmethyl amine

A. N-(2-Hydroxypropyl)benzamide

Prepare a solution of 1-amino-2-propanol (5.0 g, 66.6 mmol) in methylene chloride (250 mL) at 0° C. under nitrogen. Add Hünig's Base (11.6 mL, 66.6 mmol) followed by benzoyl chloride (7.7 mL, 66.6 mmol). Warm the reaction mixture to room temperature and stir overnight. Wash the solution sequentially with brine (100 mL) and 1M HCl (75 mL), dry (Na$_2$SO$_4$), filter, and concentrate to afford 10.0 g of N-(2-hydroxypropyl)benzamide. MS: m/e=180 (MH$^+$)

B. N-(2-Oxopropyl)benzamide

Prepare a solution of N-(2-hydroxypropyl)benzamide (8.22 g, 45.9 mmol) in methylene chloride (100 mL). Add N-methylmorpholine N-oxide (7.0 g, 60.0 mmol) followed by powdered 4 Å molecular sieves. Cool the mixture to 0° C. and add tetra-n-propylammonium perruthenate in one portion. Stir the mixture for 30 minutes and then warm to room temperature for 1 hour and filter through Celite®. Concentrate the filtrate and flash-chromatograph on silica gel eluting with 100% ethyl acetate to afford 6.1 g of N-(2-oxopropyl)benzamide as a white solid. MS: m/e=178 (MH$^+$)

C. 5-Methyl-2-phenyloxazole

Heat a solution of N-(2-oxopropyl)benzamide (1.0 g, 5.65 mmol) in concentrated H$_2$SO$_4$ (10 mL) at 100° C. for 1 hour. Cool the reaction, pour over ice, neutralize with solid Na$_2$CO$_3$, and extract with ethyl acetate (200 mL). Wash the organic phase with brine (75 mL), dry (Na$_2$SO$_4$), filter, and concentrate to afford a yellow oil. Perform flash chromatography on silica gel, eluting with 100% ethyl acetate, to afford 790 mg (88% yield) of 5-methyl-2-phenyloxazole. MS: m/e=160 (MH$^+$)

D. 5-Bromomethyl-2-phenyloxazole

Prepare a solution of 5-methyl-2-phenyloxazole (790 mg, 4.97 mmol) in CCl$_4$ (70 mL) under nitrogen. Add N-bromosuccinimide (884 mg, 4.97 mmol) and a catalytic amount of benzoyl peroxide. Reflux the mixture for 2 hours, cool to room temperature, and stir overnight. Wash the reaction mixture with a saturated solution of Na$_2$SO$_3$ (75 mL) followed by saturated sodium hydrogencarbonate (100 mL). Dry the organic phase (magnesium sulfate), filter, and concentrate to afford 1.17 g of 5-bromomethyl-2-phenyloxazole as a white solid. MS: m/e=238 (MH$^+$)

E. 2-(2-Phenyloxazol-5-ylmethyl)isoindole-1,3-dione

Dissolve 5-bromomethyl-2-phenyloxazole (1.17 g, 4.94 mmol) in dimethylformamide (15 mL) and add dropwise to a solution of potassium phthalimide (1.1 g, 5.93 mmol) in dimethylformamide (15 mL). Stir the reaction under nitrogen at room temperature overnight, concentrate to remove dimethylformamide, dissolve in ethyl acetate (75 mL), wash with saturated Na$_2$CO$_3$ (50 mL), and brine (75 mL). Dry the organic phase (Na$_2$SO$_4$), filter, and concentrate. Perform flash chromatography on silica gel eluting with 4:1 to 1:1 Hex/ethyl acetate to afford 1.5 g of 2-(2-phenyloxazol-5-ylmethyl)isoindole-1,3-dione as an off-white solid. MS: m/e=305 (MH$^+$)

F. C-(2-Phenyl-oxazol-5-yl)-methylamine

Heat a suspension of 2-(2-phenyloxazol-5-ylmethyl)isoindole-1,3-dione (1.5 g, 4.94 mmol) in 6N HCl (75 mL) at reflux for 5 days. Cool, basify with 3 N sodium hydroxide, and extract with methylene chloride (2×150 mL). Dry the organic phase (Na$_2$SO$_4$), filter, and concentrate to afford 400 mg of the title compound as a yellow oil. MS: m/e=175 (MH$^+$).

PREPARATION 18-1

C-(5-Phenyl-thiophene-2-yl)-methylamine

Prepare a solution of 4-phenyl-2-formyl thiophene (2.0 g, 11.4 mmol) in methanol (50 mL). Add NH$_4$OAc (8.75 g, 113.5 mmol) and NaCNBH$_3$ (0.5 g, 7.95 mmol). Stir the reaction mixture at room temperature under nitrogen for 3 days. Concentrate the mixture, dilute with water, basify with 1N sodium hydroxide, and extract with ethyl acetate (2×100 mL). Dry the organic phase (magnesium sulfate), filter, and concentrate. Perform flash chromatography on silica gel eluting with 9:1 ethyl acetate/MeOH to afford 100 mg of the title compound. $^1$H NMR (CDCl$_3$) δ 7.58 (d, J=8 Hz, 2H), 7.25-7.40 (m, 3H), 7.16 (d, J=4 Hz, 1H), 6.89 (d, J=4 Hz, 1H), 4.08 (s, 2H).

PREPARATION 19-1

C-(4-Phenyl-furan-3-yl)-methylamine

A. 4-Phenylfuran-3-carboxylic acid ethyl ester

Mix 4-Phenyl oxazole (3.33 g, 23.0 mmol) and ethyl phenylpropiolate (4.0 g, 23.0 mmol) in a sealed tube and heat at 220° C. for 20 hours. Perform flash-chromatography on silica gel eluting with 4:1 Hex/ethyl acetate to afford 3.9 g of 4-phenylfuran-3-carboxylic acid ethyl ester as a yellow oil. MS: m/e=217 (MH$^+$).

B. (4-Phenylfuran-3-yl)methanol

Prepare a solution of 4-phenylfuran-3-carboxylic acid ethyl ester (3.9 g, 18.1 mmol) in toluene (20 mL) under nitrogen at −78° C. Add a 1.0 M solution of Diisobutyl aluminium hydride in methylene chloride (35 mL, 35.0 mmol). Stir the reaction mixture for 1 hour, quench with water, and pour into 10% Rochelle's salt (200 mL). Extract the aqueous phase with ethyl acetate (2×200 mL). Wash the organic phase with brine (100 mL), dry ($Na_2SO_4$), filter, and concentrate. Flash chromatography on silica gel eluting with 4:1 Hex/ethyl acetate to afford 2.3 g of (4-phenylfuran-3-yl)methanol. $^1$H NMR (CDCl$_3$) δ 7.51-7.58 (m, 4H), 7.30-7.45 (m, 3H), 4.67 (d, J=5 Hz, 2H).

C. 4-Phenyl-3-formylfuran

Prepare a solution of (4-phenylfuran-3-yl)methanol (2.3 g, 13.2 mmol) in methylene chloride (20 mL). Add N-methylmorpholine N-oxide (2.2 g, 18.5 mmol) and powdered 4 Å molecular sieves. Cool the mixture to 0° C. and add tetra-n-propyl ammonium perruthenate. Warm the mixture to room temperature and stir for an additional 3 hours. Filter the reaction mixture through Celite® and concentrate the filtrate. Perform flash chromatography on silica gel eluting with 10% diethyl ether/hexane to afford 1.36 g of 4-phenyl-3-formylfuran. $^1$H NMR (CDCl$_3$) δ 10.01 (s, 1H), 8.15 (s, 1H), 7.60 (s, 1H), 7.35-7.54 (m, 5H).

D. C-(4-Phenylfuran-3-yl)methylamine

Prepare a solution of 4-phenyl-3-formylfuran (1.36 g, 7.91 mmol) in methanol (35 mL). Add NH$_4$OAc (6.1 g, 79.1 mmol) and NaCNBH$_3$ (348 mg, 5.54 mmol). Stir the reaction mixture at room temperature under nitrogen for 2.5 days then concentrate the mixture, dilute with water (50 mL), basify with 1 N sodium hydroxide, and extract with methylene chloride (2×100 mL). Dry the organic phase (Na$_2$SO$_4$), filter, and concentrate. Perform flash chromatography on silica gel eluting with 9:1 ethyl acetate/MeOH followed by 100% MeOH to afford 200 mg of the title compound. $^1$H NMR (CDCl$_3$) δ 7.52 (s, 1H), 7.30-7.46 (m, 6H), 3.87 (s, 2H).

PREPARATION 20-1

C-(4-phenylfuran-2-yl)methylamine

A. 2-Formyl-4-phenyl-furan

Prepare a solution of 4-bromo-2-formylfuran (3.7 g, 21.1 mmol) in 1,2-dimethoxyethane (148 mL). Add phenyl boronic acid (5.16 g, 42.3 mmol), K$_2$CO$_3$ (31.6 mL, 63.4 mmol), Pd$_2$(dba)$_3$ (660 mg, 0.63 mmol), and PPh$_3$ (670 mg, 2.5 mmol). Stir the reaction mixture under nitrogen for 10 minutes at room temperature. After 10 minutes, heat the mixture to 80° C. for 3 days. Wash the reaction mixture with brine (30 mL), dry (Na$_2$SO$_4$), filter, and concentrate. Perform flash chromatography on silica gel eluting with 1:1 hex/ethyl acetate to afford the title compound (1.5 g) as a brown liquid. $^1$H NMR (CDCl$_3$) δ 9.71 (s, 1H), 7.97 (s, 1H), 6.82-7.55 (m, 6H).

B. C-(4-phenyl-furan-2-yl)methylamine

Prepare a solution of 4-phenyl-2-formylfuran (1.5 g, 8.7 mmol) and MeOH (35 mL). Add NH$_4$OAc (6.7 g, 87.1 mmol) and NaCNBH$_3$ (380 mg, 6.1 mmol). Stir the reaction mixture under nitrogen for 12 hours. Upon completion of the reaction, concentrate the resulting mixture, dilute with water (10 mL), basify with 1 N sodium hydroxide, and extract with diethyl ether (2×10 mL). Dry the organic phase (Na$_2$SO$_4$), filter, and concentrate. Perform flash chromatography on silica gel eluting with 9:1 ethyl acetate/MeOH to afford the title compound (230 mg) as a white solid. $^1$H NMR (CDCl$_3$) δ 7.65 (s, 1H), 7.46 (d, J=7 Hz, 1H), 7.36 (t, J=7 Hz, 1H), 7.26 (m, 1H), 6.49 (s, 1H), 3.89 (s, 2H), 2.10 (s, 2H).

PREPARATION 21-1

C-(2-Methylthiazol-4-yl)methylamine

A. (2-Methylthiazol-4-yl)acetic acid ethyl ester

Prepare a solution of thioacetamide (10 g, 133 mmol) in ethanol (75 mL). Add ethyl-4-chloroacetoacetate (16.5 mL, 122 mmol). Stir the reaction overnight at 50° C. and then concentrate in vacuo. Dissolve the resulting oil in water (75 mL) and extract with diethyl ether (3×50 mL). Extract the aqueous layer with CHCl$_3$ (3×50 mL). Wash the combined organic layers with brine (50 mL), dry (Na$_2$SO$_4$), filter, and concentrate in vacuo to afford (2-methylthiazol-4-yl)acetic acid ethyl ester (17 g) as a solid. $^1$H NMR (CDCl$_3$) δ 7.02 (s, 1H), 4.15-4.25 (m, 2H), 3.79 (s, 2H), 2.71 (s, 3H), 1.25 (t, J=7 Hz, 3H).

B. (2-Methylthiazol-4-yl)acetic acid

Prepare a solution of (2-methylthiazol-4-yl)acetic acid ethyl ester (17 g, 92 mmol) in tetrahydrofuran/water (1:1, 400 mL). Add potassium hydroxide (10.3 g, 184 mmol). Stir the reaction at room temperature for 1 hour. Concentrate the solution in vacuo to remove the tetrahydrofuran then acidify with 1N HCl. Extract the aqueous solution with CHCl$_3$. Wash the resulting organic phase with brine (200 mL), dry (Na$_2$SO$_4$), filter and concentrate in vacuo to afford (2-methylthiazol-4-yl)acetic acid (11.3 g) as a solid. $^1$H NMR (CDCl$_3$) δ 7.00 (s, 1H), 3.85 (s, 2H), 2.71 (s, 3H).

C. (2-Methylthiazol-4-ylmethyl carbamic acid 2-trimethylsilanyl-ethyl ester Prepare a solution of (2-methylthiazol-4-yl)acetic acid (3.8 g, 22.7 mmol) in toluene (100 mL) and triethylamine (3.2 mL, 22.7 mmol). Add diphenyl phosphoryl azide (4.9 mL, 22.7 mmol). Stir the reaction at 80° C. for 2 hours and then add trimethylsilylethanol (6.5 mL, 45.5 mmol). Continue stirring at 80° C. for 1 hour, then stir at 40° C. overnight. Concentrate the resulting solution in vacuo to remove toluene and then basify with 10% sodium hydroxide (50 mL). Extract the aqueous solution with ethyl acetate (2×50 mL). Wash the combined organic phase with brine (50 mL), dry (Na$_2$SO$_4$), filter and concentrate in vacuo to a solid. Perform chromatography (silica gel, 7:3 Hex/ethyl acetate) to afford (2-methylthiazol-4-ylmethyl)carbamic acid 2-trimethylsilanyl-ethyl ester (11 g) as a solid. $^1$H NMR (CDCl$_3$) δ 6.99 (s, 1H), 5.30 (br s, 1H), 4.42 (d, J=7 Hz, 2H), 4.18 (t, J=9 Hz, 2H), 2.60 (s, 3H), 0.99 (t, J=9 Hz, 2H), 0.05 (s, 9H).

D. C-(2-Methyl-thiazol-4-yl)methylamine

Add (2-methylthiazol-4-ylmethyl)carbamic acid 2-trimethylsilanyl-ethyl ester (3.5 g, 13.1 mmol) to a 1M solution of tetrabutylammonium fluoride in tetrahydrofuran (26.2 mL). Stir at 50° C. for 2.5 hours. Concentrate the resulting solution in vacuo to an oil. Dissolve the oil in water, basify with 10% sodium hydroxide and extract with ethyl acetate (2×50 mL). Wash the combined organic layers with brine (50 mL), dry Na$_2$SO$_4$), filter and concentrate to an oil. Perform chromatography (silica gel, 93:7:1 CHCl$_3$/MeOH/ concentrated NH$_4$OH) to afford C-(2-methylthiazol-4-yl) methylamine (140 mg). MS: m/e=129 (MH+).

PREPARATION 22-1

2-Thiazol-4-yl-ethylamine

A. 2-(3-Oxobutyl)isoindole-1,3-dione

Prepare a suspension of phthalimide (5 g, 34 mmol) in ethyl acetate (40 mL). Add methyl vinyl ketone (2.8 mL, 34 mmol) followed by NaOEt (116 mg, 1.7 mmol) in ethanol (10 mL). Stir the reaction at room temperature for 2 hours, then heat to reflux and stir for 3 hours. Concentrate the reaction in vacuo to a solid. Recrystallize the solid from ethanol to afford 2-(3-oxobutyl)isoindole-1,3-dione (6.8 g). $^1$H NMR (CDCl$_3$) δ 7.82-7.88 (m, 2H), 7.69-7.77 (m, 2H), 3.97 (t, J=7 Hz, 2H), 2.88 (t, J=7 Hz, 2H), 2.20 (s, 3H).

B. 2-(4-Bromo-3-oxobutyl)isoindole-1,3-dione

Prepare a cold (0° C.) solution of 2-(3-oxobutyl)isoindole-1,3-dione (6.8 g, 31.5 mmol) in methanol (50 mL). Add Br$_2$ (3.2 mL, 63 mmol). Allow the reaction to warm to room temperature and stir for 15 hours. Add 10 M sulfuric acid (26 mL) and stir the mixture for 15 hours. Filter off the solids and dry in vacuo to afford 2-(4-bromo-3-oxobutyl)isoindole-1,3-dione (2.3 g).

$^1$H NMR (CDCl$_3$) δ 7.85-7.90 (m, 2H), 7.69-7.77 (m, 2H), 4.05 (t, J=7 Hz, 2H), 3.96 (s, 2H), 3.15 (t, J=7 Hz, 2H).

C. 2-(2-Thiazol-4-ylethyl)isoindole-1,3-dione

Reflux formamide (2 mL, 50 mmol) and P$_2$S$_5$ (4.4 g, 10 mmol) dioxane (50 mL) for 2 hours. Add this crude solution to 2-(4-bromo-3-oxobutyl)isoindole-1,3-dione (2.3 g, 7.7 mmol) in dioxane (100 mL) and reflux the resulting reaction solution for 1.5 hours. Add ethyl acetate (100 mL) and 1N sodium hydroxide (100 mL) to the mixture. Separate the organic phase, wash with brine (50 mL), dry (Na$_2$SO$_4$), filter and concentrate in vacuo to an oil. Perform chromatography (silica gel, 7:3 hexane/ethyl acetate) to afford 2-(2-thiazol-4-ylethyl)isoindole-1,3-dione (790 mg). $^1$H NMR (CDCl$_3$) δ 8.75 (s, 1H), 7.80-7.88 (m, 2H), 7.69-7.75 (m, 2H), 7.08 (s, 1H), 4.10 (t, J=7 Hz, 2H), 3.28 (t, J=7 Hz, 2H).

D. 2-Thiazol-4-ylethylamine

Prepare a solution of 2-(2-thiazol-4-ylethyl)isoindole-1, 3-dione (720 mg, 3.1 mmol) in methanol (100 mL). Add hydrazine (0.6 mL, 20 mmol). Stir the reaction at reflux for 48 hours, then at room temperature for 48 hours. Concentrate the reaction in vacuo to an oil. Perform chromatography (silica gel, 93:6:1 CHCl$_3$/MeOH/concentrated NH$_4$OH) to afford the title compound (50 mg). $^1$H NMR (CDCl$_3$) δ 8.78 (s, 1H), 7.04 (s, 1H), 3.10 (t, J=7 Hz, 2H), 2.97 (t, J=7 Hz, 2H).

PREPARATION 23-1

3-Benzoimidazol-1-yl-propylamine

Prepare a suspension of sodium hydride (812 mg, 20 mmol) in tetrahydrofuran (50 mL). Add benzimidazole (2 g, 16.9 mmol) under nitrogen. Reflux the mixture for 1 hour. At the same time, add 3-bromopropylamine hydrobromide (3.7 g, 16.9 mmol) to a suspension of sodium hydride (676 mg, 16.9 mmol) under nitrogen and reflux the mixture for 1 hour. Combine the two mixtures and reflux for 2 hours. Filter the reaction mixture, concentrate the filtrate to an oil, basify with sodium hydroxide and extract with ethyl acetate (3×50 mL). Concentrate the combined organic layers to an oil. Perform chromatography (silica gel, 9:1 methylene chloride/ MeOH) to afford the title compound (780 mg) MS: m/e=176 (MH+)

PREPARATION 24-1

C-(5-Phenylthiazol-4-yl)methylamine

A. Thiobenzoic acid O-ethyl ester

Prepare a solution of ethyl benzoate (10 g, 66.5 mmol) in xylene (100 mL). Add Lawesson's reagent (14.5 g, 36 mmol). Reflux the reaction for 5 hours, then concentrate in vacuo to an oil. Chromatograph (silica gel, 100% Hexane) to afford thiobenzoic acid O-ethyl ester (6.9 g). $^1$H NMR (CDCl$_3$) δ 8.20 (d, J=8 Hz, 2H), 7.52 (t, J=7 Hz, 1H), 7.39 (t, J=7 Hz, 2H), 4.69-4.78 (m, 2H), 1.55 (t, J=7 Hz, 3H).

B. 5-Phenylthiazole-4-carboxylic acid ethyl ester

Prepare a suspension of NaCN (0.25 g, 5.2 mmol) in ethanol (50 mL). Add dropwise ethyl isocyanoacetate (5 mL, 45.6 mmol) and thiobenzoic acid O-ethyl ester (6.9 g, 41.5 mmol) in ethanol (25 mL). Stir the reaction mixture at 50° C. for 96 hours and then concentrate in vacuo to an oil. Chromatograph (silica gel, 3:7 hexane/ethyl acetate) to afford 5-phenylthiazole-4-carboxylic acid ethyl ester (6.0 g). MS: m/e=234 (MH+).

C. (5-Phenylthiazol-4-yl)methanol

Prepare a cold (0° C.) solution of 5-phenylthiazole-4-carboxylic acid ethyl ester (3.0 g, 12.9 mmol) in tetrahydrofuran (150 mL). Add LiAlH$_4$ (488 mg, 12.9 mmol). Allow the reaction to slowly warm to room temperature and stir for 3 hours. Quench with water (25 mL) and filter through Celite®. Concentrate the filtrate in vacuo to a residue. Chromatograph (silica gel, 3:7 hexane/ethyl acetate) to afford (5-phenylthiazol-4-yl)methanol (1.4 g). $^1$H NMR (CDCl$_3$) δ 8.75 (s, 1H), 7.40-7.55 (m, 5H), 4.80 (d, J=4 Hz, 2H), 3.15-3.22 (m, 1H).

D. 4-Bromomethyl-5-phenylthiazole

Prepare a cold (0° C.) solution of (5-phenyl-thiazol-4-yl)-methanol (1.4 g, 7.3 mmol) in $CH_3CN$ (50 mL). Add $PPh_3$ (2.6 g, 9.7 mmol) and $CBr_4$ (3.2 g, 9.7 mmol). Stir the reaction at 0° C. for 3 hours, allow to warm to room temperature and then concentrate in vacuo to an oil. Chromatograph (silica gel, 4:1 Hex/ethyl acetate) to afford the title compound (400 mg). $^1H$ NMR ($CDCl_3$) δ 8.80 (s, 1H), 7.40-7.60 (m, 5H), 4.65 (s, 2H).

E. 2-(5-Phenylthiazol-4-ylmethyl)isoindole-1,3-dione

Prepare a cold (0° C.) solution of potassium phthalimide (350 mg, 1.8 mmol) in dimethylformamide (25 mL). Add dropwise 4-bromomethyl-5-phenyl-thiazole (400 mg, 1.6 mmol) in dimethylformamide (10 mL). Warm the reaction to room temperature, stir for 3 hours and then concentrate. Dissolve the residue in ethyl acetate (100 mL), wash with saturated $Na_2CO_3$ (50 mL) and brine (50 mL), then dry ($Na_2SO_4$), filter and concentrate to a brown residue. Chromatograph (silica gel, 4:1 hexane/ethyl acetate) to afford 2-(5-phenylthiazol-4-ylmethyl)isoindole-1,3-dione (270 mg).

$^1H$ NMR ($CDCl_3$) δ 8.70 (s, 1H), 7.35-7.89 (m, 9H), 5.04 (s, 2H).

F. C-(5-Phenyl-thiazol-4-yl)-methylamine

Prepare a cold (0° C.) solution of 2-(5-phenylthiazol-4-ylmethyl)isoindole-1,3-dione (260 mg, 0.8 mmol) in methanol (15 mL). Add hydrazine (0.05 mL, 1.6 mmol). Warm the reaction to room temperature and stir overnight. Concentrate the reaction in vacuo. Dissolve the residue in ethyl acetate (25 mL) and filter to remove solids. Concentrate the filtrate in vacuo to an oil. Chromatograph (silica gel, 93:6:1 $CHCl_3$/MeOH/concentrated $NH_4OH$) to afford the title compound (130 mg). $^1H$ NMR ($CDCl_3$) δ 8.75 (s, 1H), 7.39-7.49 (m, 5H), 4.00 (s, 2H), 1.62 (br s, 2H).

PREPARATION 25-1

C-(3-Phenylfuran-2-yl)methylamine

A. 3-Bromofuran-2-carbaldehyde

Prepare a solution of 3-bromofuran (0.61 mL, 6.80 mmol) in diethyl ether (10 mL) at −78° C. under nitrogen. Add lithium diisopropylamide (2M in tetrahydrofuran, 4.08 mL, 8.16 mmol) dropwise over 30 minutes. Immediately quench the reaction with dimethylformamide, allow to warm to room temperature, and wash with saturated aqueous sodium hydrogencarbonate. Extract the aqueous phase with ethyl acetate (2×10 mL), and wash the combined organic phases with brine (40 mL), dry (magnesium sulfate), filter, and concentrate. Perform flash chromatography of the resulting residue on silica gel eluting with 5:1 hexane/ethyl acetate to afford 514 mg of 3-bromofuran-2-carbaldehyde as a white solid. MS: m/e=175 [MH+].

B. 3-Phenylfuran-2-carbaldehyde

Prepare a mixture of 3-bromofuran-2-carbaldehyde (381 mg, 2.19 mmol), phenylboronic acid (534 mg, 4.38 mmol), and 2M potassium carbonate (3.28 mL, 6.57 mmol) in 1,2-dimethoxyethane (20 mL). Bubble nitrogen into this mixture for 20 minutes. Add $Pd_2(dba)_3$ (68 mg, 0.06 mmol) and $PPh_3$ (68 mg, 0.26 mmol) and purge the mixture with nitrogen for an additional 10 minutes. Then heat the mixture to 80° C. After 24 hours, evaporate the solvent and redissolve the residue in ethyl acetate. Extract the aqueous phase with ethyl acetate (2×10 mL), wash the combined organic phases with brine (40 mL), dry (magnesium sulfate), filter and concentrate. Perform flash chromatography on silica gel eluting with 5:1 hex/ethyl acetate to afford 405 mg of the title compound as a white solid. MS: m/e=173 [MH+]

C. C-(3-Phenylfuran-2-yl)methylamine

Stir a solution of 3-phenylfuran-2-carbaldehyde (401 mg, 2.33 mmol) and $NH_4OAc$ (1.79 g, 23.30 mmol) in methanol (8 mL) at room temperature under nitrogen. Add $NaCNBH_3$ (102 mg, 1.63 mmol). After stirring at room temperature for 24 hours, concentrate the mixture, dilute with water (2 mL), basify with 1N sodium hydroxide, and extract with diethyl ether (4×10 mL). Dry the combined organic phases (magnesium sulfate), filter and concentrate. Perform flash chromatography on silica gel eluting with 9:1 ethyl acetate/MeOH to afford 37 mg of the title compound as a yellow solid. $^1H$ NMR ($CDCl_3$) δ 7.19-7.41 (m, 6H), 6.49 (d, J=2 Hz, 1H), 3.95(s, 2H), 1.80 (br s, 2H).

PREPARATION 26-1

C-(5-Phenylthiophen-3-yl)methylamine

A. 5-Bromothiophene-3-carboxylic acid

Prepare a solution of thiophene carboxylic acid (500 mg, 3.90 mmol) in HOAc (5 mL). Add $Br_2$ (0.17 mL, 0.85 mmol), in HOAc (3 mL), dropwise. Then stir the mixture for 15 minutes at room temperature under nitrogen. Quench the reaction with ice cold water and stir for an additional 10 minutes. Cool the solution −10° C. when the product will precipitate out. Filter the solution, rinse the filter cake with ice cold water, and dry the product to afford 473 mg of 5-bromothiophene-3-carboxylic acid as a white solid. $^1H$ NMR (dimethylsulfoxide-$d_6$) δ 12.90 (br s, 1H), 8.18 (d, J=1.5 Hz, 1H), 7.46 (d, J=1.5 Hz, 1H).

B. 5-Bromothiophene-3-carboxylic acid methyl ester

Prepare a solution of 5-bromothiophene-3-carboxylic acid (500 mg, 2.41 mmol) in methanol (5 mL). Add concentrated hydrochloric acid (0.1 mL). Reflux the mixture for 3 hours, cool to room temperature, pour into water, and extract with diethyl ether (3×10 mL). Wash the combined organic phases with water (10 mL), then saturated aqueous sodium hydrogencarbonate (10 mL). Dry (magnesium sulfate), filter and concentrate. Perform flash chromatography on silica gel eluting with 5:1 hexane/ethyl acetate to afford 409 mg of 5-bromothiophene-3-carboxylic acid methyl ester as a white solid. $^1H$ NMR ($CDCl_3$) δ 8.10 (d, J=1.5 Hz, 1H), 7.17 (d, J=1.5 Hz, 1H), 3.86 (s, 3H).

C. 5-Phenylthiophene-3-carboxylic acid methyl ester

Prepare a mixture of 5-bromo-thiophene-3-carboxylic acid methyl ester (1.86 g, 8.41 mmol), phenylboronic acid (2.05 g, 16.83 mmol), and 1 M aqueous potassium carbonate (12.5 mL, 25.23 mmol) in 1,2-dimethoxyethane (70 mL) and purge with nitrogen for 20 minutes. Add Pd(PPh$_3$)$_4$ (485 mg, 0.42 mmol) and again purge the mixture with nitrogen for 10 minutes. Heat to 80° C. for 24 hours. Evaporate the solvent and redissolve the residue in ethyl acetate. Extract the aqueous phase with ethyl acetate (2×20 mL), wash the combined organic phases brine (40 mL), dry (magnesium sulfate), filter and concentrate. Perform flash chromatography on silica-gel eluting with 10:1 hexane/ethyl acetate to afford 947 mg of 5-phenylthiophene-3-carboxylic acid methyl ester as a white solid. MS: m/e=219 [MH+].

D. (5-Phenylthiophene-3-yl)methanol

Prepare a solution of 5-phenylthiophene-3-carboxylic acid methyl ester (500 mg, 2.29 mmol) in tetrahydrofuran (30 mL) and cool to 0° C. under nitrogen. Slowly add LiAl$_4$ (1 M in tetrahydrofuran). After stirring for 1 hour at 0° C., quench the reaction with water, filter through Celite®, and rinse with ethyl acetate. Concentrate the filtrate to afford 416 mg of (5-phenylthiophene-3-yl)methanol as a white solid. $^1$H NMR (CDCl$_3$) δ7.60-7.61 (m, 2H), 7.25-7.37 (m, 4H), 7.16 (s, 1H), 4.69 (d, J=2 Hz, 2H), 1.58 (μm, 1H).

E. 4-Bromomethyl-2-phenylthiophene

Prepare a solution of (5-phenylthiophene-3-yl)methanol (394 mg, 2.07 mmol) in tetrahydrofuran (30 mL). Cool to 0° C. under nitrogen. Add PPh$_3$ (723 mg, 2.75 mmol). Add dropwise a solution of carbon tetrabromide (912 mg, 2.75 mmol) in CH$_3$CN (15 mL). Stir the reaction at 0° C. for 2 hours, then warm to room temperature overnight. Concentrate the mixture and flash-chromatograph on silica gel eluting with 7:3 ethyl acetate/hexane to afford 515 mg of 4-bromomethyl-2-phenylthiophene as a white solid. MS: m/e=254 [MH+].

F. 2-(5-Phenylthiophen-3-ylmethyl)isoindole-1,3-dione

Prepare a solution of potassium phthalimide (457 mg, 2.47 mmol) in dimethylformamide (6 mL). Add a solution of 4-bromomethyl-2-phenyl-thiophene (523 mg, 2.06 mmol) in dimethylformamide (6 mL), dropwise. Stir the reaction mixture overnight at room temperature under nitrogen. Concentrate the solution, redissolve in ethyl acetate, wash with saturated aqueous sodium hydrogencarbonate (20 mL), then brine (20 mL). Dry (magnesium sulfate), filter aid concentrate. Preform flash chromatography of the resulting residue on silica gel eluting with 5:1 hexane/ethyl acetate to afford 565 mg of 2-(5-phenylthiophen-3-ylmethyl)isoindole-1,3-dione as a yellow solid. $^1$H NMR (CDCl$_3$) δ 7.84-7.88 (m, 2H), 7.70-7.72 (m, 2H0, 7.54-7.57 (m, 2H), 7.25-7.34 (m, 5H), 4.83 (s, 2H).

G. C-(5-Phenylthiophen-3-yl)methylamine

Prepare a solution of 2-(5-phenylthiophen-3-ylmethyl)isoindole-1,3-dione (565 mg, 1.77 mmol) in methanol (57 mL). Add hydrazine (0.35 mL, 11.14 mmol). Heat the mixture to reflux. After stirring for 1 hour, cool the mixture to room temperature and concentrate. Perform flash chromatography on silica gel eluting with 50:40:9:1 methylene chloride/CHCl$_3$/MeOH/concentrated NH$_4$OH to afford 280 mg of the title compound as a yellow solid. MS: m/e=190 [MH+].

PREPARATION 27-1

2,5-Dimethyl-2H-pyrazole-3-carbaldehyde

Dissolve ethyl-3-methylpyrazole-5-carboxylate (1.0893 g, 7.07 mmol) in 10 mL tetrahydrofuran and add it dropwise to a suspension of sodium hydride (60%) (377.6 mg, 9.44 mmol) in 10 mL tetrahydrofuran. After 2 hours, quench the reaction with methyl iodide (excess) and stir for an additional 2 hours. Add water to the reaction and remove the tetrahydrofuran in vacuo. Partition the residue between ethyl acetate and brine. Dry the organic layer with magnesium sulfate. Filter and remove the solvent in vacuo to afford 950.0 mg of crude 2,5-dimethyl-2H-pyrazole-3-carboxylic acid ethyl ester. Dissolve this material (950.0 mg, 5.65 mmol) in 10 mL tetrahydrofuran and add it dropwise to a slurry of lithium aluminum hydride (220.2 mg) in 20 mL tetrahydrofuran at 0° C. After 30 minutes at this temperature, heat the reaction to reflux for 2 hours. Cool the reaction to room temperature and add 20 mL ethyl acetate to the reaction. Add 5N sodium hydroxide to the reaction until a white precipitate appears. Filter the reaction and concentrate the filtrate in vacuo. Partition the residue between ethyl acetate and water. Dry the organic layer with magnesium sulfate. Filter and remove the solvent in vacuo to afford 493.7 mg of crude (2,5-dimethyl-2H-pyrazol-3-yl)-methanol. Dissolve this crude material (493.7 mg, 3.91 mmol) in 20 mL methylene chloride and add MnO$_2$ (1.2939 g, 14.88 mmol) to the reaction mixture. Heat the reaction mixture to reflux and allow it to stir for 16 hours. Cool the reaction and filter it through a pad of celite. Concentrate the filtrate in vacuo to afford 444.5 mg of crude product. Purify via Biotage chromatography (25% ethyl acetate/Hexanes) to afford 138.7 mg of the title compound $^1$H NMR (CDCl3) δ 9.81 (1H, s), 6.46 (1H, s), 3.82 (3H, s), 2.24 (3H, s).

PREPARATION 28-1

5-Methylfuran-2-carbaldehyde

To a tetrahydrofuran solution (150 mL) of 1-methylpiperazine (3.3 g, 32.81 mmol, 1.05 eq) under argon at −78° C., slowly add a solution of n-butyllitium (13.12 mL, 2.5 M in hexanes, 32.81 mmol, 1.05 eq). Stir at −78° C. for 15 minutes and then slowly add furan-2-carbaldehyde (3.0 g, 31.25 mmol, 1 eq). Stir at −78° C. for 20 minutes and then slowly add a solution of sec-butyl lithium (25.24 mL, 1.3 M in hexanes, 32.81 mmol, 1.05 eq). Stir solution at −78° C. for 1 hour. Add more tetrahydrofuran (150 mL) to aid in stirring. Stir for an additional 2 hours and slowly add iodomethane (17.7 g, 125 mmol, 4 eq). Slowly warm to room temperature overnight. Pour reaction into a 10:1 mixture of 10% hydrochloric acid:ice and stir. Add diethyl ether and extract product into organics. Separate organics, dry with magnesium sulfate, and concentrate on rotovap. Purify on Fluorisil to give 485 mg of 5-methyl-furan-2-carbaldehyde.

EXAMPLE 1-1

3-Fluorobiphenyl-4-carboxylic acid (R)-(6-((3-ethoxypropylamino)methyl)-2R-hydroxyindan-1-yl) amide

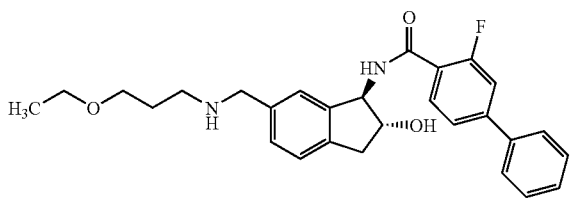

A. (R)-(2R-Hydroxy-6-iodoindan-1-yl)carbamic acid tert-butyl ester

Combine (R)-(6-amino-2R-hydroxyindan-1-yl)carbamic acid tert-butyl ester (5.0 g, 18.9 mmol) and 100 mL of diiodomethane under $N_2$. Add isoamylnitrite (11 g, 94.5 mmol, 12.7 mL) to this stirring solution. Stir this solution at room temperature for 1 hour and then heat to 7° C. and stir for an additional hour. Cool reaction and remove diiodomethane on high vacuum rotovap at 60-70° C. Dissolve the crude in dichloromethane and purify on silica gel to give 3.92 g of (R)-(2R-hydroxy-6-iodoindan-1-yl)carbamic acid tert-butyl ester as a yellow powder.

B. (R)-(6-Ethyl-2R-hydroxyindan-1-yl)carbamic acid tert-butyl ester

Combine (R)-(2R-hydroxy-6-iodoindan-1-yl)carbamic acid tert-butyl ester (4 g, 10.66 mmol) and tetrakis(triphenylphosphine)palladium(0) (616 mg, 0.53 mmol) under $N_2$ and add 100 mL dry dioxane. Add tributyl(vinyl)tin (3.72 g, 11.73 mmol, 3.4 mL) to the stirring solution and heat to 75° C. Stir solution overnight at 75° C. Cool solution and remove solvent on rotovap. Add ethyl acetate to the crude material followed by approximately 50 mL of a saturated aqueous potassium fluoride solution. Stir vigorously for 2 hours and filter the biphasic mixture through a shallow bed of celite in a fritted glass funnel. Separate organics and wash them several times with water and finally with brine before drying organics with magnesium sulfate. Remove solvents on rotovap to give 5.84 g of crude and purify on silica gel. This gives 2.3 g of (R)-(6-ethyl-2R-hydroxyindan-1-yl)carbamic acid tert-butyl ester. MS (m/e): 276.9 (MH+).

C. (R)-(6-Formyl-2R-hydroxyindan-1-yl)carbamic acid tert-butyl ester

Dissolve (R)-(6-ethyl-2R-hydroxyindan-1-yl)carbamic acid tert-butyl ester (2.3 g, 8.35 mmol, 1 eq) in 60 mL of a 2:1 methylene chloride:methanol solution. Cool solution to −78° C. via a dry ice/acetone bath. Introduce $O_3$ to the cold solution via gas dispersion tube for 15 minutes. Stop $O_3$ flow and purge solution with $N_2$ for 15 minutes at −78° C. Slowly add methyl sulfide (1.04 g, 16.7 mmol, 1.226 mL, 2 eq) to the solution. Slowly warm solution to room temperature and remove solvent on rotovap to give 3.5 g of a crude oil. Purify this material by silica gel chromatography. This gives 1.86 g of (R)-(6-formyl-2R-hydroxyindan-1-yl)carbamic acid tert-butyl ester. MS (m/e): 276 (MH−).

D. (R)-(6-(3-Ethoxypropylamino)methyl-2R-hydroxyindan-1-yl)carbamic acid tert-butyl ester Combine (R)-(6-formyl-2R-hydroxyindan-1-yl)carbamic acid tert-butyl ester (1.0 g, 3.6 mmol, 1 eq) and 30 mL of 1,2-dichloroethane under $N_2$. Add 3-ethoxypropylamine (558 mg, 5.41 mmol, 648 μL, 1.5 eq) at room temperature and stir solution for 10 minutes. Add sodium triacetoxyborohydride (1.146 g, 5.41 mmol, 1.5 eq) and stir reaction overnight at room temperature. Remove solvent on rotovap. Dissolve crude material in methanol and treat with hydroxide anion exchange resin (AG 1-X8 resin, 20-50 mesh hydroxide form, cat # 140-1422 from Bio Rad) until basic to pH paper. Stir for 5 minutes before filtering off resin. Remove methanol on rotovap. Add additional methanol and repeat rotoevaportation. Purify crude by silica gel chromatography to give 884 mg (67% yield) of (R)-(6-(3-ethoxypropylamino)methyl-2R-hydroxyindan-1-yl)carbamic acid tert-butyl ester. MS (m/e): 365.3 (MH+).

E. 3-Fluorobiphenyl-4-carboxylic acid (R)-(6-(3-ethoxypropylamino)methyl-2R-hydroxyindan-1-yl) amide At 0° C. under $N_2$, combine (6-(3-ethoxypropylamino)methyl-2-hydroxyindan-1-yl)carbamic acid tert-butyl ester (877 mg, 2.41 mmol, 1 eq) and 5 mL trifluoroacetic acid. Stir the cold solution for 30 minutes. Remove trifluoroacetic acid on the rotovap. Dissolve crude material in methanol and treat with hydroxide anion exchange resin (AG 1-X8 resin, 20-50 mesh hydroxide form, cat # 140-1422 from Bio Rad) until basic to pH paper. Stir for 5 minutes before filtering off resin. Remove methanol on rotovap. Add additional methanol and repeat rotoevaportation to give the free base. Add 3-fluorobiphenyl-4-carboxylic acid 2,5-dioxopyrrolidin-1-yl ester (739 mg, 2.23 mmol, 1.08 eq) to the free base and under $N_2$ add 10 mL dry dimethylformamide. Stir overnight at room temperature. Remove dimethylformamide on high vacuum rotovap and dissolve crude in methanol and again treat with the hydroxide resin until basic. Stir for 5 minutes, filter off resin, and remove methanol on rotovap. Purify the crude material by silca gel chromatography to give the title compound (823 mg) MS (m/e): 463 (MH+).

EXAMPLES 1-2 THROUGH 1-18 ARE PREPARED ESSENTIALLY AS EXAMPLE 1-1

| Ex. # | Compound Name | Data (MS) |
|---|---|---|
| 1-2 | Biphenyl-4-carboxylic acid (R)-(6-(2-ethoxyethylamino)methyl-2R-hydroxyindan-1-yl)amide | 431.2 (M + H)+ |
| 1-3 | 3-Fluorobiphenyl-4-carboxylic acid (R)-(6-(2-ethoxyethylamino)methyl-2R-hydroxyindan-1-yl)amide | 449.2 (M + H)+ |

| Ex. # | Compound Name | Data (MS) |
|---|---|---|
| 1-4 | 2'-Fluoro-4'-trifluoromethylbiphenyl-4-carboxylic acid (R)-(6-(2-ethoxyethylamino)methyl-2R-hydroxyindan-1-yl)amide | 517.2 (M + H)+ |
| 1-5 | Biphenyl-4-carboxylic acid (R)-(6-(morpholin-4-yl)methyl-2R-hydroxyindan-1-yl)amide | 429.2 (M + H)+ |
| 1-6 | Biphenyl-4-carboxylic acid (R)-(6-(4-methylpiperazin-1-yl)methyl-2R-hydroxyindan-1-yl)amide | 442.2 (M + H)+ |
| 1-7 | Biphenyl-4-carboxylic acid (R)-(6-(furan-2-ylmethylamino)methyl-2R-hydroxyindan-1-yl)amide | 439.2 (M + H)+ |
| 1-8 | 3-Fluorobiphenyl-4-carboxylic acid (R)-(6-(thien-2-ylmethylamino)methyl-2R-hydroxyindan-1-yl)amide | 473.2 (M + H)+ |
| 1-9 | 3-Fluorobiphenyl-4-carboxylic acid (R)-(6-(2-propoxyethylamino)methyl-2R-hydroxyindan-1-yl)amide | 463.3 (M + H)+ |
| 1-10 | 3,2'-Difluorobiphenyl-4-carboxylic acid (R)-(6-(3-ethoxypropylamino)methyl-2R-hydroxyindan-1-yl)amide | 481.2 (M + H)+ |
| 1-11 | 3-Fluoro-2'-trifluoromethylbiphenyl-4-carboxylic acid (R)-(6-(3-ethoxypropylamino)methyl-2R-hydroxyindan-1-yl)amide | 531.3 (M + H)+ |
| 1-12 | 3-Fluorobiphenyl-4-carboxylic acid (R)-(6-(2-(1-ethylpyrrolidin-2-yl)ethylamino)methyl-2R-hydroxyindan-1-yl)amide | 488.3 (M + H)+ |
| 1-13 | 3-Fluoro-2'-methylbiphenyl-4-carboxylic acid (R)-(6-(3-ethoxypropylamino)methyl-2R-hydroxyindan-1-yl)amide | 477.3 (M + H)+ |
| 1-14 | 3-Fluoro-2'-methylbiphenyl-4-carboxylic acid (R)-(6-(3-(imidazol-1-yl)propylamino)methyl-2R-hydroxyindan-1-yl)amide | 499.3 (M + H)+ |
| 1-15 | Biphenyl-4-carboxylic acid (R)-(6-((4-fluorophenyl)methylamino)methyl-2R-hydroxyindan-1-yl)amide | 467 (M + H)+ |
| 1-16 | Biphenyl-4-carboxylic acid (R)-(6-(2-(4-fluorophenyl)ethylamino)methyl-2R-hydroxyindan-1-yl)amide | 481 (M + H)+ |
| 1-17 | 3-Fluorobiphenyl-4-carboxylic acid (R)-(6-((pyridin-2-yl)methylamino)methyl-2R-hydroxyindan-1-yl)amide | 468 (M + H)+ |
| 1-18 | 3-Fluorobiphenyl-4-carboxylic acid (R)-(6-(2-(pyridin-4-yl)ethylamino)methyl-2R-hydroxyindan-1-yl)amide | 482 (M + H)+ |

EXAMPLE 2-1

3-Fluorobiphenyl-4-carboxylic acid (R)-(6-(3-isopropoxypropylamino)methyl-2R-hydroxyindan-1-yl)amide

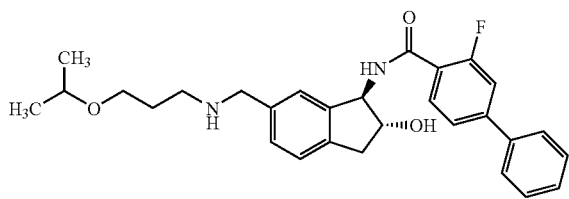

A. (R)-(2R-Hydroxy-6-iodo)indan-1-yl-ammonium trifluoroacetate

Add (2-hydroxy-6-iodoindan-1-yl)carbamic acid tert-butyl ester (8.67 g, 23.12 mmol) to a 0° C. solution of trifluoroacetic acid (50 mL). Stir for 1 hour. Evaporate the solvent to give a solid. Suspend the solid in toluene (75 mL) and re-evaporate to afford 10.8 g of the title compound.

B. 3-Fluorobiphenyl-4-carboxylic acid (R)-(2R-hydroxy-6-iodoindan-1-yl)amide Add a solution of oxalyl chloride (3.22 g, 25.43 mmol) in methylene chloride (8 mL) dropwise to a 0° C. suspension of 3-fluorobiphenyl-4-carboxylic acid (5 g 23.13 mmol) in methylene chloride (100 mL). Then warm the suspension to 23° C. and stir for 2 hours. Slowly add the resulting acid chloride solution over 15 minutes to a 23° C., biphasic mixture of (R)-(2R-hydroxy-6-iodoindan-1-yl-ammonium trifluoroacetate (10.8 g, 23.12 mmol), Na$_2$CO$_3$ (12.25 g, 115.8 mmol), methylene chloride (60 mL), and water (60 mL). Stir the reaction mixture for 2 hours and then filter. Rinse the filtered solids with water. Separate the filtrate layers and evaporate the organic layer to yield additional solids. Combine these solids with the filtered solids, suspend in acetonitrile (150 mL), and stir for 15 hours at 23° C. Filter the suspension and dry the solids to afford 8.58 g of 3-fluorobiphenyl-4-carboxylic acid (R)-(2R-hydroxy-6-iodoindan-1-yl)amide as a tan solid. A second crop yields an additional 0.95 g. MS (m/z): 474 (M+1).

C. 3-Fluorobiphenyl-4-carboxylic acid (R)-(2R-hydroxy-6-vinylindan-1-yl)amide Heat a suspension of 3-fluorobiphenyl-4-carboxylic acid (R)-(2R-hydroxy-6-iodoindan-1-yl)amide (5 g, 10.56 mmol), tributyl(vinyl)tin (3.58 g, 11.3 mmol), tetrakis(triphenylphosphine)Pd(0) (0.61 g, 0.52 mmol), and dioxane (125 mL) for 4 hours at 75° C. Cool the reaction mixture and evaporate the solvent to afford a residue. Suspend the residue in ethyl acetate (125 mL), then heat at reflux for 15 minutes, cool to 0° C., and filter. Stir the filtrate for 15 minutes with a solution of potassium fluoride (46 g) and water (50 mL). Then filter the mixture was through a pad of Celite. Separate the filtrate layers and wash the ethyl acetate layer sequentially with water (100 mL) and then saturated brine (100 mL). Dry the ethyl acetate layer over sodium sulfate and evaporate the solvent to afford a residue. Purify the residue on a flash column (80/20 methylene chloride/ethyl acetate) to afford 2.19 g of purified 3-fluorobiphenyl-4-carboxylic acid (R)-(2R-hydroxy-6-vinylindan-1-yl) amide (55%). MS (m/z): 374.2 (M+1).

D. 3-Fluorobiphenyl-4-carboxylic acid (R)-(6-formyl-2R-hydroxyindan-1-yl)amide Dissolve 3-fluorobiphenyl-4-carboxylic acid (R)-(2R-hydroxy-6-vinylindan-1-yl)amide (1.94 g, 5.18 mmol, 1 eq) in 100 mL of a 1:1 methylene chloride:methanol solution. Cool solution to −78° C. via a dry ice/acetone bath. Introduce $O_3$ to the cold solution via gas dispersion tube for 10 minutes. Stop $O_3$ flow and purge solution with $N_2$ for 15 minutes at −78° C. Slowly add methyl sulfide (1.04 g, 16.7 mmol, 1.226 mL, 2 eq) to the solution. Slowly warm solution to room temperature and remove solvent on rotovap to give 2.18 g crude product. Purify this material by silica gel chromatography. This gives 1.423 g of 3-fluorobiphenyl-4-carboxylic acid (R)-(6-formyl-2R-hydroxyindan-1-yl)amide. MS (m/e): 376.2 (MH+).

E. 3-Fluorobiphenyl-4-carboxylic acid (R)-(6-(3-isopropoxypropylamino)methyl-2R-hydroxyindan-1-yl)amide Combine 3-fluorobiphenyl-4-carboxylic acid (R)-(6-formyl-2R-hydroxyindan-1-yl)amide (50 mg, 0.133 mmol, 1 eq) and 3 mL of 1,2-dichloroethane under $N_2$. Add 3-isopropoxypropylamine (23 mg, 0.199 mmol, 26 μL, 1.5 eq) at room temperature and stir the solution for 10 minutes. Add sodium triacetoxyborohydride (42 mg, 0.199 mmol, 1.5 eq) and stir the reaction overnight at room temperature. Remove the solvent on rotovap and dissolve the crude product in ethyl acetate. Purify the crude product by silica gel chromatography to give 49 mg of the title compound. MS (m/e): 477.3 (MH+).

EXAMPLES 2-2 THROUGH 2-63 ARE PREPARED ESSENTIALLY AS EXAMPLE 2-1

| Ex. # | Compound Name | Data (MS) |
| --- | --- | --- |
| 2-2 | 3-Fluorobiphenyl-4-carboxylic acid (R)-(6-(3-phenylpropylamino)methyl-2R-hydroxyindan-1-yl)amide | 495 (M + H)+ |
| 2-3 | 3-Fluorobiphenyl-4-carboxylic acid (R)-(6-(4-phenylbutylamino)methyl-2R-hydroxyindan-1-yl)amide | 509 (M + H)+ |
| 2-4 | 3-Fluorobiphenyl-4-carboxylic acid (R)-(6-(benzylamino)methyl-2R-hydroxyindan-1-yl)amide | 467 (M + H)+ |
| 2-5 | 3-Fluorobiphenyl-4-carboxylic acid (R)-(6-(3-(pyridin-3-yl)propylamino)methyl-2R-hydroxyindan-1-yl)amide | 496 (M + H)+ |
| 2-6 | 3-Fluorobiphenyl-4-carboxylic acid (R)-(6-(2-(thien-2-yl)ethylamino)methyl-2R-hydroxyindan-1-yl)amide | 487 (M + H)+ |
| 2-7 | 3-Fluorobiphenyl-4-carboxylic acid (R)-(6-(2-(1-methylimidazol-5-yl)ethylamino)methyl-2R-hydroxyindan-1-yl)amide | 485 (M + H)+ |
| 2-8 | 3-Fluorobiphenyl-4-carboxylic acid (R)-(6-(3-(6-methylpyridin-2-yl)propylamino)methyl-2R-hydroxyindan-1-yl)amide | 510 (M + H)+ |
| 2-9 | 3-Fluorobiphenyl-4-carboxylic acid (R)-(6-(4-(3-methoxypropyl)piperazin-1-yl)methyl-2R-hydroxyindan-1-yl)amide | 518 (M + H)+ |
| 2-10 | 3-Fluorobiphenyl-4-carboxylic acid (R)-(6-(3-(imidazol-1-yl)propylamino)methyl-2R-hydroxyindan-1-yl)amide | 485 (M + H)+ |
| 2-11 | 3-Fluorobiphenyl-4-carboxylic acid (R)-(6-(3-(methylthio)propylamino)methyl-2R-hydroxyindan-1-yl)amide | 465 (M + H)+ |
| 2-12 | 3-Fluorobiphenyl-4-carboxylic acid (R)-(6-(cyclohexylmethylamino)methyl-2R-hydroxyindan-1-yl)amide | 473 (M + H)+ |
| 2-13 | 3-Fluorobiphenyl-4-carboxylic acid (R)-(6-(tert-butoxypropylamino)methyl-2R-hydroxyindan-1-yl)amide | 491 (M + H)+ |
| 2-14 | 3-Fluorobiphenyl-4-carboxylic acid (R)-(6-(2-(2-methylthien-5-yl)ethylamino)methyl-2R-hydroxyindan-1-yl)amide | 501 (M + H)+ |
| 2-15 | 3-Fluorobiphenyl-4-carboxylic acid (R)-(6-(2-(3-fluorophenyl)ethylamino)methyl-2R-hydroxyindan-1-yl)amide | 499 (M + H)+ |
| 2-16 | 3-Fluorobiphenyl-4-carboxylic acid (R)-(6-(2-(2-fluorophenyl)ethylamino)methyl-2R-hydroxyindan-1-yl)amide | 499 (M + H)+ |
| 2-17 | 3-Fluorobiphenyl-4-carboxylic acid (R)-(6-(2-phenylpropylamino)methyl-2R-hydroxyindan-1-yl)amide | 495 (M + H)+ |
| 2-18 | 3-Fluorobiphenyl-4-carboxylic acid (R)-(6-(2-phenoxyethylamino)methyl-2R-hydroxyindan-1-yl)amide | 497 (M + H)+ |
| 2-19 | 3-Fluorobiphenyl-4-carboxylic acid (R)-(6-(1H-pyrazol-3-ylamino)methyl-2R-hydroxyindan-1-yl)amide | 443 (M + H)+ |
| 2-20 | 3-Fluorobiphenyl-4-carboxylic acid (R)-(6-(1-methyl-1H-pyrazol-3-ylamino)methyl-2R-hydroxyindan-1-yl)amide | 471 (M + H)+ |
| 2-21 | 3-Fluorobiphenyl-4-carboxylic acid (R)-(6-(2-(4-phenylimidazol-1-yl)ethylamino)methyl-2R-hydroxyindan-1-yl)amide | 547 (M + H)+ |
| 2-22 | 3-Fluorobiphenyl-4-carboxylic acid (R)-(6-((2-phenyl-[1,3,4]oxadiazol-5-yl)methylamino)methyl-2R-hydroxyindan-1-yl)amide | 535 (M + H)+ |

-continued

| Ex. # | Compound Name | Data (MS) |
|---|---|---|
| 2-23 | 3-Fluorobiphenyl-4-carboxylic acid (R)-(6-((2-phenylimidazol-1-yl)ethylamino)methyl-2R-hydroxyindan-1-yl)amide | 443 (M + H)+ |
| 2-24 | 3-Fluorobiphenyl-4-carboxylic acid (R)-(6-(2-(4-fluorophenyl)ethylamino)methyl-2R-hydroxyindan-1-yl)amide | 499 (M + H)+ |
| 2-25 | 3-Fluorobiphenyl-4-carboxylic acid (R)-(6-(2-(3-chlorophenyl)ethylamino)methyl-2R-hydroxyindan-1-yl)amide | 495 (M + H)+ |
| 2-26 | 3-Fluorobiphenyl-4-carboxylic acid (R)-(6-(1-phenylcycloprop-2-ylamino)methyl-2R-hydroxyindan-1-yl)amide | 493 (M + H)+ |
| 2-27 | 3-Fluorobiphenyl-4-carboxylic acid (R)-(6-(2-(4-methylphenyl)ethylamino)methyl-2R-hydroxyindan-1-yl)amide | 495 (M + H)+ |
| 2-28 | 3-Fluorobiphenyl-4-carboxylic acid (R)-(6-((2-(4-fluorophenylthio)ethyl)methylamino)methyl-2R-hydroxyindan-1-yl)amide | 545 (M + H)+ |
| 2-29 | 3-Fluorobiphenyl-4-carboxylic acid (R)-(6-((2-(phenylthio)ethyl)methylamino)methyl-2R-hydroxyindan-1-yl)amide | 527 (M + H)+ |
| 2-30 | 3-Fluorobiphenyl-4-carboxylic acid (R)-(6-(2-(phenylthio)ethylamino)methyl-2R-hydroxyindan-1-yl)amide | 513 (M + H)+ |
| 2-31 | Biphenyl-4-carboxylic acid (R)-(6-((4-fluorophenyl)amino)methyl-2R-hydroxyindan-1-yl)amide | 453 (M + H)+ |
| 2-32 | Biphenyl-4-carboxylic acid (R)-(6-((3-fluorophenyl)amino)methyl-2R-hydroxyindan-1-yl)amide | 453 (M + H)+ |
| 2-33 | Biphenyl-4-carboxylic acid (R)-(6-((2-fluorophenyl)amino)methyl-2R-hydroxyindan-1-yl)amide | 453 (M + H)+ |
| 2-34 | Biphenyl-4-carboxylic acid (R)-(6-((n-pentyl)methylamino)methyl-2R-hydroxyindan-1-yl)amide | 443 (M + H)+ |
| 2-35 | Biphenyl-4-carboxylic acid (R)-(6-(phenylamino)methyl-2R-hydroxyindan-1-yl)amide | 435 (M + H)+ |
| 2-36 | Biphenyl-4-carboxylic acid (R)-(6-(3-(pyridin-2-yl)propylamino)methyl-2R-hydroxyindan-1-yl)amide | 478 (M + H)+ |
| 2-37 | Biphenyl-4-carboxylic acid (R)-(6-(3-(pyridin-3-yl)propylamino)methyl-2R-hydroxyindan-1-yl)amide | 478 (M + H)+ |
| 2-38 | Biphenyl-4-carboxylic acid (R)-(6-(3-(pyridin-4-yl)propylamino)methyl-2R-hydroxyindan-1-yl)amide | 478 (M + H)+ |
| 2-39 | Biphenyl-4-carboxylic acid (R)-(6-(2-(pyridin-2-ylthio)ethylamino)methyl-2R-hydroxyindan-1-yl)amide | 496 (M + H)+ |
| 2-40 | Biphenyl-4-carboxylic acid (R)-(6-((2-methyl-1,3-thiazol-5-yl)methylamino)methyl-2R-hydroxyindan-1-yl)amide | 470 (M + H)+ |
| 2-41 | Biphenyl-4-carboxylic acid (R)-(6-((2-methyl-1,3-oxazol-5-yl)methylamino)methyl-2R-hydroxyindan-1-yl)amide | 454 (M + H)+ |
| 2-42 | 3-Fluorobiphenyl-4-carboxylic acid (R)-(6-(2-(1,3-thiazol-2-yl)ethylamino)methyl-2R-hydroxyindan-1-yl)amide | 486 (M + H)+ |
| 2-43 | 3-Fluorobiphenyl-4-carboxylic acid (R)-(6-((2-phenyl-1,3-oxazol-5-yl)methylamino)methyl-2R-hydroxyindan-1-yl)amide | 534 (M + H)+ |
| 2-44 | 3-Fluorobiphenyl-4-carboxylic acid (R)-(6-((2-phenylthien-5-yl)methylamino)methyl-2R-hydroxyindan-1-yl)amide | 549 (M + H)+ |
| 2-45 | 3-Fluorobiphenyl-4-carboxylic acid (R)-(6-((3-phenylfuran-4-yl)methylamino)methyl-2R-hydroxyindan-1-yl)amide | 533 (M + H)+ |
| 2-46 | 3-Fluorobiphenyl-4-carboxylic acid (R)-(6-((biphen-2-yl)methylamino)methyl-2R-hydroxyindan-1-yl)amide | 543 (M + H)+ |
| 2-47 | 3-Fluorobiphenyl-4-carboxylic acid (R)-(6-((3-phenylfuran-5-yl)methylamino)methyl-2R-hydroxyindan-1-yl)amide | 533 (M + H)+ |
| 2-48 | Biphenyl-4-carboxylic acid (R)-(6-(3-(morpholin-4-yl)propylamino)methyl-2R-hydroxyindan-1-yl)amide | 486 (M + H)+ |
| 2-49 | 3-Fluorobiphenyl-4-carboxylic acid (R)-(6-(2-methyl-1,3-thiazol-4-yl)methylamino)methyl-2R-hydroxyindan-1-yl)amide | 488 (M + H)+ |
| 2-50 | 3-Fluorobiphenyl-4-carboxylic acid (R)-(6-(2-(1,3-thiazol-4-yl)ethylamino)methyl-2R-hydroxyindan-1-yl)amide | 488 (M + H)+ |
| 2-51 | 3-Fluorobiphenyl-4-carboxylic acid (R)-(6-(2-(benzimidazol-1-yl)ethylamino)methyl-2R-hydroxyindan-1-yl)amide | 535 (M + H)+ |
| 2-52 | 3-Fluorobiphenyl-4-carboxylic acid (R)-(6-((biphen-4-yl)methylamino)methyl-2R-hydroxyindan-1-yl)amide | 543 (M + H)+ |
| 2-53 | 3-Fluorobiphenyl-4-carboxylic acid (R)-(6-((biphen-3-yl)methylamino)methyl-2R-hydroxyindan-1-yl)amide | 543 (M + H)+ |
| 2-54 | 3-Fluorobiphenyl-4-carboxylic acid (R)-(6-((5-phenyl-1,3-thiazol-4-yl)methylamino)methyl-2R-hydroxyindan-1-yl)amide | 550 (M + H)+ |
| 2-55 | Biphenyl-4-carboxylic acid (R)-(6-(3-(2-oxopyrrolidin-1-yl)propylamino)methyl-2R-hydroxyindan-1-yl)amide | 484 (M + H)+ |

-continued

| Ex. # | Compound Name | Data (MS) |
|---|---|---|
| 2-56 | Biphenyl-4-carboxylic acid (R)-(6-((biphen-3-yl)methylamino)methyl-2R-hydroxyindan-1-yl)amide | 525 (M + H)+ |
| 2-57 | Biphenyl-4-carboxylic acid (R)-(6-((biphen-4-yl)methylamino)methyl-2R-hydroxyindan-1-yl)amide | 525 (M + H)+ |
| 2-58 | Biphenyl-4-carboxylic acid (R)-(6-((biphen-2-yl)methylamino)methyl-2R-hydroxyindan-1-yl)amide | 525 (M + H)+ |
| 2-59 | 4-Bromo-2-fluorophenyl-1-carboxylic acid (R)-(6-((isopropyl)methylamino)methyl-2R-hydroxyindan-1-yl)amide | 435, 437 (M + H)+ |
| 2-60 | 3-Fluorobiphenyl-4-carboxylic acid (R)-(6-((2-bromofuran-5-yl)methylamino)methyl-2R-hydroxyindan-1-yl)amide | 535 (M + H)+ |
| 2-61 | 3-Fluorobiphenyl-4-carboxylic acid (R)-(6-((2-ethylfuran-5-yl)methylamino)methyl-2R-hydroxyindan-1-yl)amide | 485 (M + H)+ |
| 2-62 | 3-Fluorobiphenyl-4-carboxylic acid (R)-(6-((6-fluoropyridin-2-ylthio)ethylamino)methyl-2R-hydroxyindan-1-yl)amide | 535 (M + H)+ |
| 2-63 | Biphenyl-4-carboxylic acid (R)-(6-((6-fluoropyridin-2-ylthio)ethylamino)methyl-2R-hydroxyindan-1-yl)amide | 514 (M + H)+ |

EXAMPLE 3-1

3-Fluorobiphenyl-4-carboxylic acid (R)-(6-(2-phenylethylamino)methyl-2R-hydroxyindan-1-yl)amide

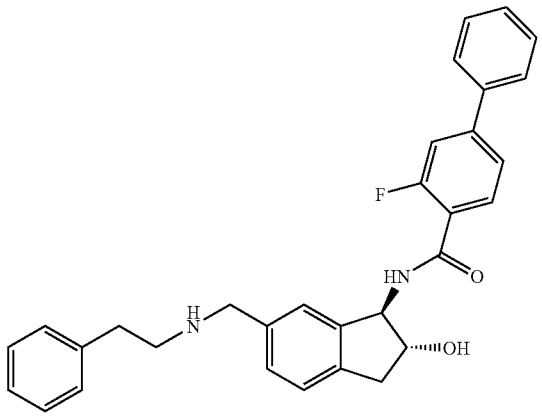

Stir 3-fluorobiphenyl-4-carboxylic acid (6-formyl-2-hydroxyindan-1-yl)amide (1 equivalent, 50 mg), 4-phenethylamine (1.5 equivalent, 24 mg), and titanium isopropoxide (2.0 equivalent, 75 mg) in ethanol until completion. Add sodium borohydride (1.5 equivalent, 12 mg) to the reaction mixture and stir until completion. Concentrate the reaction mixture. Dilute the residue with dichloromethane and wash with 1 M sodium hydroxide. Dry the organic layer over magnesium sulfate and concentrate. Purify the residue via flash column chromatography with a mixture of methanol in dichloromethane to afford 20 mg of the title compound as solid material (28% yield). MS (m/e): 481.3 (M+).

EXAMPLES 3-2 THROUGH 3-5 ARE PREPARED ESSENTIALLY AS EXAMPLE 3-1

| Ex. # | Compound Name | Data (MS) |
|---|---|---|
| 3-2 | 3-Fluorobiphenyl-4-carboxylic acid (R)-(6-((piperidin-4-yl)methylamino)methyl-2R-hydroxyindan-1-yl)amide | 474(M + H)+ |
| 3-3 | 3-Fluorobiphenyl-4-carboxylic acid (R)-(6-(2-(1-methylimidazol-4-yl)ethylamino)methyl-2R-hydroxyindan-1-yl)amide | 485(M + H)+ |
| 3-4 | 3-Fluorobiphenyl-4-carboxylic acid (R)-(6-(2-(pyridin-3-yl)ethylamino)methyl-2R-hydroxyindan-1-yl)amide | 482(M + H)+ |
| 3-5 | 3-Fluorobiphenyl-4-carboxylic acid (R)-(6-(2-(2-phenylfuran-5-yl)ethylamino)methyl-2R-hydroxyindan-1-yl)amide | 547(M + H)+ |

EXAMPLE 4-1

3-Fluorobiphenyl-4-carboxylic acid (R)-(6-aminomethyl-2R-hydroxyindan-1-yl)amide

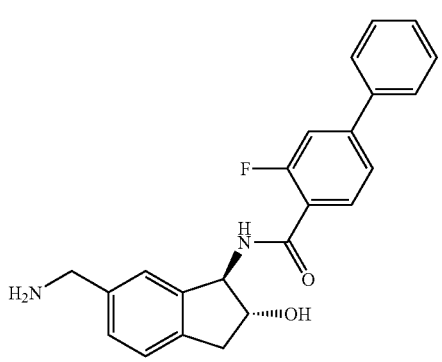

Charge a flame dried flask with sodium cyanide (693 mg, 14.1 mmol) and 15 mL dimethylsulfoxide. Add copper cyanide (1.05 g, 11.7 mmol) and stir vigorously under Ar overnight. A homogeneous green brown solution is obtained. In a separate flask, dissolve 3-fluorobiphenyl-4-carboxylic acid (R)-(6-amino-2R-hydroxyindan-1-yl)amide in 30 mL tetrahydrofuran and cool to 0° C. Add boron trifluoride diethyl etherate (0.478 mL, 3.77 mmol) followed by t-butyl nitrite (0.413 mL, 3.53 mmol). Stir the reaction at 0° C. for 1 hour, add 100 mL of cold hexane and filter the resulting precipitate, wash with additional hexane, and quickly re-dissolve in 20 mL of dimethylsulfoxide. Add this dimethylsulfoxide solution dropwise to the $NaCu(CN)_2$ solution over a period of 5 minutes with vigorous stirring. Stir the reaction for 15 minutes more, dilute with water and extract with ethyl acetate (3×). Dry organics over magnesium sulfate, filter and evaporate onto silica gel. Purification by flash column chromatography (ethyl acetate, Hexanes) gives 636 mg of 3-fluorobiphenyl-4-carboxylic acid (R)-(6-cyano-2R-hydroxyindan-1-yl)amide. MH− 371.7.

Combine 3-fluorobiphenyl-4-carboxylic acid (R)-(6-cyano-2R-hydroxyindan-1-yl)amide (473 mg, 1.27 mmol), ethanol (30 mL) and concentrated HCl (3.0 mL). Evacuate the flask and back fill with hydrogen. Stir the reaction overnight at room temperature. Dilute reaction with water (30 mL) and tetrahydrofuran (30 mL) to dissolve any precipitate. Filter reaction through celite. Add 5 M sodium hydroxide to the aqueous portion until basic by pH paper and extract with ethyl acetate. Dry the organic layer with magnesium sulfate, filter, and evaporate to give the title compound as a white solid (454 mg). MS: 375.1 (MH−).

EXAMPLE 5-1

3-Fluorobiphenyl-4-carboxylic acid (R)-(6-(((6-bromopyridin-2-yl)methylamino)methyl)-2-R-hydroxy-indan-1-yl)amide

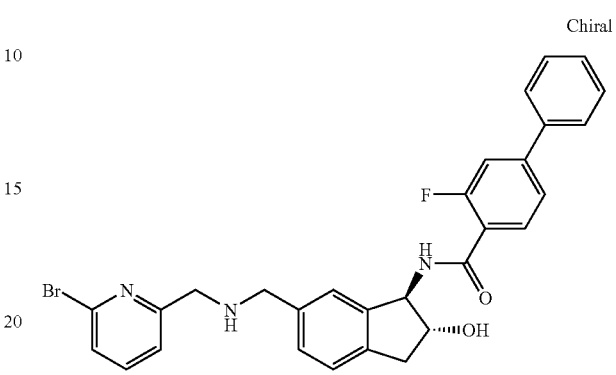

Combine 3-fluorobiphenyl-4-carboxylic acid (R)-(6-aminomethyl-2R-hydroxyindan-1-yl)amide (50 mg, 0.132 mmol) and 6-bromopyridine-2-carbaldehyde (24 mg, 0.132 mmol) in tetrahydrofuran (1.0 mL). Add sodium tri(acetoxy)borohydride (63 mg, 0.198 mmol) and stir at room temperature overnight. Dilute reaction with saturated sodium hydrogencarbonate and extract with ethyl acetate ×3. Pool organics, dry over magnesium sulfate, filter, and evaporate onto silica gel. Purify by flash column chromatography (MeOH, ethyl acetate, Hexanes) to give 33 mg of the title compound. MS: 546.0 (MH+).

EXAMPLES 5-2 THROUGH 5-4 ARE PREPARED ESSENTIALLY AS EXAMPLE 5-1

| Ex. # | Compound Name | Data (MS) |
| --- | --- | --- |
| 5-2 | 3-Fluorobiphenyl-4-carboxylic acid (R)-(6-((5-methylthien-2-yl)methylamino)methy)-2R-hydroxyindan-1-yl)amide | 487(M + H)+ |
| 5-3 | 3-Fluorobiphenyl-4-carboxylic acid (R)-(6-((5-phenylfuran-2-yl)methylamino)methyl)-2R-hydroxyindan-1-yl)amide | 534(M + H)+ |
| 5-4 | 3-Fluorobiphenyl-4-carboxylic acid (R)-(6-((5-methylfuran-2-yl)methylamino)methyl)-2R-hydroxyindan-1-yl)amide | 471(M + H)+ |

EXAMPLE 6-1

3-Fluorobiphenyl-4-carboxylic acid (R)-(6-((2,5-dimethyl-2H-pyrazol-3-yl)methylamino)methyl-2-R-hydroxyindan-1-yl)amide Dissolve 3-fluorobiphenyl-4-carboxylic acid (R)-(6-aminomethyl-2R-hydroxyindan-1-yl)amide (51.6 mg, 0.137 mmol) and 2,5-dimethyl-2H-pyrazole-3-carbaldehyde (17.5 mg, 0.141 mmol) in 3 mL absolute ethanol. Add triethylamine (27.73 mg, 0.274 mmol) and titanium(IV) isopropoxide (77.89 mg, 0.274 mmol) to the reaction mixture and allow it to stir for 24 hours at room temperature. Add sodium borohydride (19.3 mg, 0.510 mmol) to the reaction mixture and allow it to stir for 4 hours. Concentrate the reaction mixture in vacuo and partition the residue between methylene chloride and 1N sodium hydroxide. Dry the organic layer with magnesium sulfate. Filter and remove the solvent in vacuo to afford 33.1 mg of crude product. Purify the crude material via silica gel chromatography (5% MeOH/CHCl$_3$) to afford 20.1 mg of the title product MS (m/e): 485.2 (M+1).

EXAMPLE 6-2 IS PREPARED ESSENTIALLY AS EXAMPLE 6-1

| Ex. # | Compound Name | Data (MS) |
|---|---|---|
| 6-2 | 3-Fluorobiphenyl-4-carboxylic acid (R)-(6-((2-(4-fluorophenyl)furan-2-yl)methylamino)methyl-2R-hydroxyindan-1-yl)amide | 551(M + H)+ |

EXAMPLE 7-1

3,2'-Difluorobiphenyl-4-carboxylic acid (R)-(6-((3-ethoxypropyl)methylamino)methyl-2-R-hydroxyindan-1-yl)amide

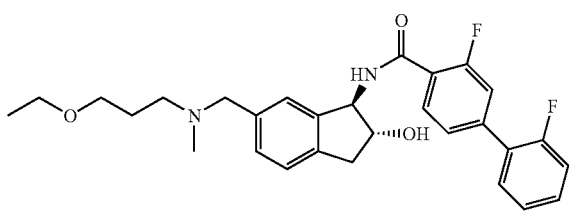

Add 3,2'-Difluorobiphenyl-4-carboxylic acid (R)-(6-(3-ethoxypropylamino)methyl-2R-hydroxyindan-1-yl)amide (20 mg, 0.04 mmol), formaldehyde (25 mg, 0.83 mmol), and formic acid (100 mg, 2.08 mmol) to a test tube. Heat the solution at 95° C. overnight. Add water followed by a few drops of ammonium hydroxide to the reaction and extract product into ethyl acetate. Separate organics and dry over magnesium sulfate. Purify crude on silica gel to give 12 mg of the title compound. MS (m/e): 495.3 (MH+).

EXAMPLES 7-2 THROUGH 7-4 ARE PREPARED ESSENTIALLY AS EXAMPLE 7-1

| Ex. # | Compound Name | Data (MS) |
|---|---|---|
| 7-2 | 5-Fluorobiphenyl-4-carboxylic acid (R)-(6-((3-ethoxypropyl)methylamino)methyl-2R-hydroxyindan-1-yl)amide | 477.3(MH+) |
| 7-3 | 3-Fluoro-2'-methylbiphenyl-4-carboxylic acid (R)-(6-((3-ethoxypropyl)methylamino)methyl-2R-hydroxyindan-1yl)amide- | 491.3(MH+) |
| 7-4 | 3-Fluoro-2'-methylbiphenyl-4-carboxylic acid (R)-(6-((3-(1H-pyrazol-1-yl)propyl)methylamino)methyl-2R-hydroxyindan-1-yl)amide | 513.2(MH+) |

EXAMPLE 8-1

3-Fluorobiphenyl-4-carboxylic acid (R)-(6-((3-ethoxypropyl)ethylamino)methyl-2R-hydroxyindan-1-yl)amide

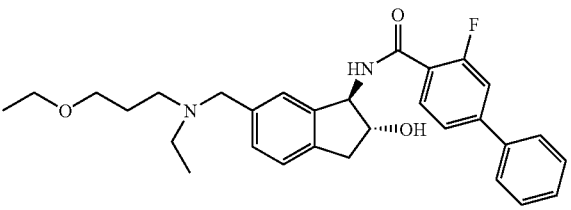

Combine 3-fluorobiphenyl-4-carboxylic acid (R)-(6-(3-ethoxypropylamino)methyl-2R-hydroxyindan-1-yl)amide (50 mg, 0.108 mmol, 1 eq) and 5 mL of 1,2-dichloroethane under N$_2$. Add acetaldehyde (about 1 mL) followed by sodium triacetoxyborohydride (34 mg, 0.162 mmol, 1.5 eq) and stir reaction overnight at room temperature. Remove solvent on rotovap and dissolve crude in methanol. Add hydroxide anion exchange resin (AG 1-X8 resin, 20-50 mesh hydroxide form, cat # 140-1422 from Bio Rad) until basic to pH paper. Stir for 5 minutes before filtering off resin. Remove methanol on rotovap. Add additional methanol and repeat rotoevaportation to give 80 mg crude material. Purify crude by silica gel chromatography to give 19 mg of the title compound as a yellow oil. MS (m/e): 491.3 (MH+).

EXAMPLES 8-2 THROUGH 8-5 AREPREPARED

ESSENTIALLY AS EXAMPLE 8-1

| Ex. # | Compound Name | Data (MS) |
| --- | --- | --- |
| 8-2 | 3-Fluorobiphenyl-4-carboxylic acid (R)-(6-((3-ethoxypropyl)isopropylamino)methyl-2R-hydroxyindan-1-yl)amide | 505.4(MH+) |
| 8-3 | 3-Fluorobiphenyl-4-carboxylic acid (R)-(6-((3-ethoxypropyl)propylamino)methyl-2R-hydroxyindan-1-yl)amide | 505.3(MH+) |
| 8-4 | 3-Fluorobiphenyl-4-carboxylic acid (R)-(6-((3-ethoxypropyl)benzylamino)methyl-2R-hydroxyindan-1-yl)amide | 553.2(MH+) |
| 8-5 | Biphenyl-4-carboxylic acid (6-(((2-ethoxyethyl)methylamino)methyl)-2R-hydroxyindan-1-yl)amide | 445.2(MH+) Verify MS |

EXAMPLES 9-1

3-Fluorobiphenyl-4-carboxylic acid (R)-(6-((benzothiophen-2-yl)methylamino)methyl-2R-hydroxyindan-1-yl)amide

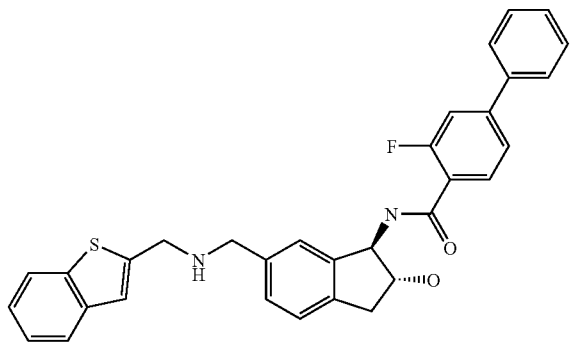

Combine 3-fluorobiphenyl-4-carboxylic acid (6-aminomethyl-2-hydroxyindan-1-yl)amide (43 mg, 0.11 mmol), 2-chloromethyl-benzothiophene (21 mg, 0.11 mmol) and tetrabutylammonium bromide (3 mg) in 1.0 mL acetonitrile and heat at 50° C. for 3 days. Cool reaction to room temperature and purify by flash column chromatography (ethyl acetate/hexanes) to give title compound. MS: 523.0 MH+.

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be Formulated and administered in the form of their pharmaceutically acceptable salts, for purposes of stability, convenience, solubility, and the like. In practice, the compounds of Formula I are usually administered in the form of pharmaceutical compositions, that is, in admixture with pharmaceutically acceptable carriers or diluents.

Thus, the present invention provides pharmaceutical compositions comprising a compound of Formula I and a pharmaceutically acceptable diluent. The present invention also provides suitable packaging, including a label, containing the pharmaceutical compositions comprising a compound of Formula I.

The compounds of Formula I can be administered by a variety of routes. In effecting treatment of a patient afflicted with disorders described herein, a compound of Formula I can be administered in any form or mode which makes the compound bioavailable in an effective amount, including oral and parenteral routes. For example, compounds of Formula I can be administered orally, by inhalation, subcutaneously, intramuscularly, intravenously, transdermally, intranasally, rectally, occularly, topically, sublingually, buccally, and the like. Oral administration is generally preferred for treatment of the disorders described herein.

One skilled in the art of preparing Formulations can readily select the proper form and mode of administration depending upon the particular characteristics of the compound selected, the disorder or condition to be treated, the stage of the disorder or condition, and other relevant circumstances. (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of oral and parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of Formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical Formulations may contain a concentration of the Formula I or its pharmaceutical salt from about 0.1 to about 10% w/v (weight per unit volume).

The compounds of Formula I are agonists of the M-1 muscarinic receptors. Moreover the compounds of Formula I are selective agonists of that particular muscarinic receptor. The compounds of the present invention possess particularly useful properties related to their bioavailability, pharmacokinetics, safety, and efficacy. Muscarinic agonists, including their subtype binding profile, can be identified by the methods that are well known in the art.

In one embodiment, the present invention provides methods of treating disorders associated with muscarinic receptors, comprising: administering to a patient in need thereof an effective amount of a compound of Formula I. Thus, the present invention contemplates the various disorders described to be treated herein and others which can be treated by such agonists as are appreciated by those skilled in the art.

A number of the disorders which can be treated by muscarinic agonists are known according to established and accepted classifications, while others are not. For example, cognition is a complicated and sometimes poorly defined phenomenon. It is, however, widely recognized that cognition includes various "domains." These domains include short term memory, long term memory, working memory, executive function, and attention.

It is understood that the compounds of the present invention are useful for treatment of disorders characterized by a deficit in any of the cognitive domains listed above or in other aspects of cognition. Thus the term "cognitive disorders" is meant to encompass any disorder characterized by a deficit in one or more cognitive domain, including but not limited to short term memory, long term memory, working memory, executive function, and attention.

One cognitive disorder to be treated by the present invention is age-related cognitive decline. This disorder is not well defined in the art, but includes decline in the cognitive domains, particularly the memory and attention domains, which accompany aging. Another cognitive disorder is mild cognitive impairment. Again, this disorder is not well defined in the art, but involves decline in the cognitive domains, and is believed to represent a group of patients the majority of which have incipient Alzheimer's disease. Another cognitive disorder is cognitive impairment associated with schizophrenia. The relationship between cognitive disturbances and other symptoms of schizophrenia is not clearly understood at present. It has been observed that some people experience cognitive problems much before they develop positive symptoms, while others acquire cognitive deterioration after the first episode and with subsequent relapses. Yet another cognitive disorder is chemotherapy-induced cognitive impairment. People who undergo cancer chemotherapy may experience a decline in cognitive function and this decline can be long lasting. Also, a wide variety of insults, including stroke, ischemia, hypoxia, inflammation, infectious processes and cognitive deficits subsequent to cardiac bypass surgery and grafting, stroke, cerebral ischemia, spinal cord trauma, head trauma, perinatal hypoxia, fetal alcohol syndrome, cardiac arrest, and hypoglycemic neuronal damage, vascular dementia, multi-infarct dementia, amylotrophic lateral sclerosis, chemotherapy, and multiple sclerosis can result in cognitive deficits as a sequella which can be treated according to the present invention.

Where the disorders which can be treated by muscarinic agonists are known according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

In particularly preferred embodiments, the present invention provides methods of treating disorders selected from the group consisting of: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia and schizophreniform disorder), dementia (including Alzheimer's disease, AIDS-induced dementia, vascular dementia, and dementia lacking distinctive histology), Parkinson's disease, Huntington's Chorea, pain (including acute pain and chronic pain), xerostomia (dry mouth), Lewy body disease (including diffuse Lewy body disease), aphasia (including primary aphasia and primary aphasia syndromes), aphasia (including primary aphasia and primary aphasia syndromes), hypotensive syndromes, and chronic colitis (including Crohn's disease), comprising: administering to a patient in need thereof an effective amount of a compound of Formula I. That is, the present invention provides for the use of a compound of Formula I or pharmaceutical composition thereof for the treatment disorders associated with muscarinic receptors.

It is recognized that the terms "treatment" and "treating" are intended to include improvement of the symptomatology associated with each of the disorders associated with muscarinic receptors described herein. Also, it is also recognized that one skilled in the art may affect the disorders by treating a patient presently afflicted with the disorders or by prophylactic ally treating a patient believed to be susceptible to such disorders with an effective amount of the compound of Formula I. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders.

It is understood that the present invention includes adjunctive treatment of the disorders described herein. More specifically, the compounds of Formula I are useful to treat disorders in which a cognitive deficit is one of the symptoms in combination with a wide variety of other therapeutic agents, in particular, in combination with AMPA potentiators; with typical and atypical antipsychotics, including olanzapine; with a variety of agents such as mGluR agonists, with NMDA antagonists, with IL 1-6 inhibitors, with other cholinergics, including cholinesterase inhibitors, such as tacrine and donepezil, and compounds that inhibit amyloid protein processing, including inhibitors of amyloid precursor protein processing and antibodies directed against amyloid proteins; with antidepressants, including SSRIs and SNRIs such as fluoxetine, paroxetine, and venlafaxine; and with anxiolytic agents; etc. It is believed that the combinations above are synergistically beneficial providing efficacy at doses that are a small fraction of those required to produce the same effect with the individual components.

In accordance with the adjunctive treatments described above, the present invention also provides a product containing a compound of Formula I and one or more therapeutic agents selected from the group consisting of AMPA potentiators; typical and atypical antipsychotics, including olanzapine; mGluR agonists; NMDA antagonists; IL 1-6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents as a combined preparation for simultaneous, separate or sequential administration in the treatment of disorders in which a cognitive deficit is one of the symptoms. In another embodiment the present invention also provides for the use of a compound of Formula I together with one or more therapeutic agents selected from AMPA potentiators; typical and atypical antipsychotics, including olanzapine; mGluR agonists; NMDA antagonists; IL 1-6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents for the manufacture of a medicament as a combined preparation for simultaneous, separate or sequential administration in the treatment of disorders in which a cognitive deficit is one of the symptoms.

As used herein, the term "simultaneous, separate or sequential administration" means that the two or more therapeutic agents are administered within a time frame which ensures that all of the therapeutic agents will provide some therapeutic activity at a particular point in time. That is to say, the therapeutic activities should at least overlap to some degree although they need not be coterminus.

As used herein, the term "patient" includes a mammal which is afflicted with one or more disorders associated with muscarinic receptors. It is understood that guinea pigs, dogs, cats, rats, mice, horses, cattle, sheep, pigs, and humans are examples of animals within the scope of the meaning of the term.

As used herein, the term "effective amount" of a compound of Formula I refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of Formula I, a number of factors are considered by the attending diagnostician, including, but not limited to: the compound of Formula I to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.01 milligram per kilogram of body weight per day (mg/kg/day) to about 50 mg/kg/day, and preferable from 0.1 milligram per kilogram of body weight per day (mg/kg/day) to about 20 mg/kg/day. More preferred amounts can be determined by one skilled in the art.

Of the disorders to be treated according to the present invention a number are particularly preferred. Particularly preferred disorders include the treatment of cognitive disorders (particularly mild cognitive impairment and cognitive impairment associated with schizophrenia), Alzheimer's disease, and psychosis, including schizophrenia.

A number of preclinical laboratory animal models have been described for the disorders described herein.

EXAMPLE A

Radial Arm Maze

The delayed non-match to sample task has been used to study the effect of drugs on memory retention (Pussinen, R. and Sirvio, J., Journal of Psychopharmacology, 13, pg.

171-179 (1999); Staubli, U., et al., Proceedings of the National Academy of Sciences, 91, pg. 777-781 (1994)) in the eight arm radial maze.

Well-trained rats were allowed to retrieve food rewards from four randomly selected arms of the maze (sampling phase). Some time later, the rats were exposed to eight open arms and were tested for their ability to remember and avoid the arms they had previously entered to obtain food. Re-entry into an arm that was baited during the sampling session was counted as a reference error, whereas entry into the same arm more than once during the retention session was counted as working error. The total (reference+working) number of errors made during the retention test increases with increasing delay periods. For example, young male rats made 0.66 (+0.4) errors at a 1 minute delay, 2 (+0.5) errors at a one hour delay, and 3.95 (+0.2) errors at a seven hour delay (observations of this lab).

Male Sprague-Dawley rats were individually housed and maintained on a 12 h light-dark cycle (lights on at 6 am). The rats were given free access to water and maintained at 85% of their free-feeding weight by supplemental feedings of Purina Lab Chow.

The rats were initially trained to search for food at the end of each of the eight arms. Once the rats had reached the criteria of no more than two errors (i.e. entering the same arm more than once during a session) on three consecutive days, a delay of one minute was imposed between the fourth and the fifth arm choices. This training ensured that the rats were thoroughly familiar with the procedural aspects of the task before any drugs were administered. Once stable performance had been obtained on the delay task (i.e. no more than one error was made on three consecutive days), drug and vehicle tests commenced using a seven hour delay period. A novel set of arms was baited each day for each rat and the maze was thoroughly cleaned during the delay period.

During the sampling session, each rat was placed on the center platform with access to all eight arms of the maze blocked. Four of the eight arms were randomly selected and baited with food. The gates of the baited arms were raised and the rat was allowed five minutes to obtain the food at the end of each of the four arms. As soon as the rat had obtained the food, it was removed, administered vehicle or various doses of compounds, and placed back in its home cage. Seven hours later (retention session), the rat was placed back onto the center platform with access to all eight arms blocked. The four arms that were previously baited during the sampling session, were baited and the gates to all eight arms were raised. The rat was allowed five minutes to obtain the remaining four pieces of food. An entry into a non-baited arm or a re-entry into a previously visited arm was counted as an error. Significance (p<0.05) was determined using a repeated measure ANOVA followed by a Dunnett's test for comparison with control.

In order to compare test compounds with standards, scopolamine and tacrine were administered s.c. immediately after the sampling phase. The effects of scopolamine, a known amnesic, were tested after a three-hour delay, whereas the effect of tacrine, a cholinesterase inhibitor used in the treatment of Alzheimer's disease was tested after a six-hour delay. Scopolamine disrupted retention after a three-hour delay in a dose-related fashion. Tacrine significantly improved retention after a six-hour delay at 10, but not at 3 mg/kg.

EXAMPLE B

Acquisition in the Radial Maze 8-Arm Radial Maze Acquisition

A prominent early feature of Alzheimer's disease (AD) symptomology is a pronounced deficit in declarative memory (R. W. Parks, R. F. Zec & R. S. Wilson eds., Neuropsychology of Alzheimer's Disease and Other Dementias, pg. 3-80 (Oxford University Press, New York) (1993)).

As the disease progresses, other domains of cognition become severely affected as well. Among the brain regions affected early in the progression of Alzheimer's disease is the hippocampus, which is a critical neural substrate for declarative memory. Differences in the pattern of hippocampal neuronal loss in normal aging and Alzheimer's disease. Lancet, 344, pg. 769-72 (1994). One behavioral test that is often used to assess hippocampal function in animal models is the 8-arm radial maze (Olton D. S., The Radial Arm Maze as a Tool in Behavioral Pharmacology, Physiology & Behavior, 40 pg. 793-97 (1986)).

Lesions or pharmacological blockade of the hippocampus disrupt performance of this task. Moreover, aged animals generally show deficits in this task (Porsolt R. D., Roux S. & Wettstein J. G., Animal Models of Dementia, Drug Development Research, 35, pg. 214-29 (1995)).

In this test of spatial learning and memory, a hungry rat is placed in the center of the maze and allowed to traverse the maze in search of food located at the end of each runway arm. In this version of the maze, the rat learns a win-shift strategy in which a visited arm is not replaced. Therefore, the most efficient foraging strategy is to visit each arm once. The version of the maze also taps into general learning processes as the rat is naïve to the maze on day one of the four day experiment.

Upon arrival, male Sprague Dawley®, rats were individually housed in a regular light-cycle colony room and allowed to acclimate for at least 4 days prior to testing. Each rat was reduced to and maintained at 85% of their target body weight throughout the experiment. Proper body weight was maintained by adjusting the allotment of lab chow based on a combination of age and the rat's daily bodyweight reading.

A session began with an individual rat being placed into the hub of the maze and then all guillotine doors were raised, allowing free access to all areas of the maze. A food hopper was located at the end of each of the 8 runway arms and a single food pellet was placed in each food hopper. Each daily session terminated when either all 8 food-hoppers had been visited or when the rat timed out (15 min on Day 1:5 min on Days 2-4). The number of arm entries was recorded. Errors were counted as repeat arm entries or failures to visit an arm in the session period. An animal was excluded from the study if it failed to visit at least one arm on Day 1, 2 arms on Day 2, and at least 4 arms on Days 3 & 4.

Each rat was pseudo-randomly assigned to either a vehicle or drug group and received the same treatment throughout the experimental period. Vehicle consisted of 5% acacia within sterile water. Injections were administered subcutaneously 20-30 minutes prior to each daily session.

In this acquisition task, vehicle-treated animals do not consistently show significant acquisition of maze learning as compared to the number of errors committed on Day 1. We have found that in compounds that facilitate acquisition of maze learning, the effects are often not observed until the fourth day of training. Therefore, results consisted of total Day 4 errors across treatment groups.

EXAMPLE C

Functional Mobilization of Intracellular Calcium

CHO cells expressing muscarinic subtypes (M1-M5) are grown as monolayers in DMEM:F-12 (3:1), 10% FBSnz, 20 mM HEPES, 1% pen/strep, 250 µg/mL G418 (GibcoBRL #10131-027). Cells are maintained under 95%/5% $O_2/CO_2$ and passaged every 3-4 days. Cells are plated 24 hours in advance of the assay at a density of 50,000/well and 48 hours in advance at a density of 25,000/well (100 µL/well) in Costar black-walled, clear-bottomed 96 well plates (Costar #3603). Cells are then incubated with minimum essential medium containing the cytoplasmic $Ca^{2+}$ indicator, Fluo-3 (1 mM Fluo mixed 1:1 with 20% pluronic acid, then diluted to 5 µM final concentration in growth and supplemented with 2.5 mM, 50 µL/well) at 37° C. in an environment containing 5% $CO_2$ for 60 minutes. Cells are washed twice with 100 µL/well of wash buffer containing Hanks Balanced Salt Solution (HBSS) without phenol red (1×) (GibcoBRL #14065-056), 20 mM HEPES (Sigma #P8761), and Probenecid (2.5 mM) (100×:1:100). For the assay, 100 µL is added to each well (100 µL of 2× drug will be added by the FLIPR). Plates are washed three times using a LabSystems multidrop and residual buffer is removed. Plates are also blotted on paper towels to remove remaining compound.

Compounds are prepared 2× (100 µL of drug added to 100 µL of assay buffer present in the well) in assay buffer containing 2% dimethylsulfoxide, HBSS without phenol red (1×) (GibcoBRL #14065-056), 20 mM HEPES (Sigma #P8761), and Probenecid (2.5 mM) (100×:1:100).

The plates were then placed into a FLIPR instrument (fluorometric imaging plate reader system, Molecular Devices, Sunnyvale, Calif.) to monitor cell fluorescence ($\lambda_{EX}$=488 nm, $\lambda_{EM}$=540 nm) before and after the addition of compounds.

The selectivity of the M1 agonists are evaluated by screening across the other muscarinic receptor subtypes (M2, M3, M4 and M5) in a similar manner. Compounds are also screened across a number of protein targets as well as the structurally related G protein-coupled receptor (GPCR) targets to insure selectivity for the M1 receptor.

EXAMPLE D

Functional GTP Binding

Cell Culture: CHO cells transfected with human M1-M5 receptors were grown either in suspension or in monolayer. For suspension cultures cells were grown in roller bottles with constant agitation at 37° C. and 5% $CO_2$ using Dulbecco's modified Eagles medium/F-12 (3:1) culture medium supplemented with 5% fetal bovine serum, 50 µg/mL tobramycin, and 20 mM HEPES. Monolayer cultures were grown in T-225 flasks at 37° C. and 5% CO2 in Dulbecco's modified Eagles medium supplemented with 10% fetal bovine serum and 100,000 U/liter of penicillin/streptomycin. Cells were harvested using trypsin-free dissociation media at 95% confluence and were collected by centrifugation and stored at 80° C. Cells stably expressing human muscarinic receptors were obtained from the National Institutes of Health.

Membrane Preparation: Cell pellets were thawed and resuspended in 20 volumes of 20 mM sodium phosphate buffer, pH 7.4, and were homogenized twice for 30 seconds at high speed using a Tissuemizer. Homogenates were centrifuged at 200 g for 15 minutes at 4° C. The supernatant was removed and reserved on ice. This procedure was repeated twice and the pooled supernatants were then centrifuged at 40,000 g for 45 minutes at 4° C. Membranes were suspended at 5 mg protein/mL and were stored at 80° C. Unless indicated otherwise in the figure legends, membranes from M1, M2, and M4 cells were prepared from cells grown in suspension, whereas those from M3 and M5 cells were from cells grown in monolayer. Receptor densities (pmol mg1 membrane protein) were 9.3, 0.7, 0.6, 0.9, and 4.8 for M1-M5 receptors, respectively.

Striatal tissue from male Sprague-Dawley rats was homogenized by hand in 10 volumes of 10 mM HEPES and 1 mM EGTA, pH 7.4, containing Complete protease inhibitor cocktail, 1 mM dithiothreitol, and 10% sucrose. The homogenate was diluted 6-fold and centrifuged at 1000 g for 10 minutes at 4° C. The supernatant was saved and the pellet rehomogenized and centrifuged as above. The combined supernatants were centrifuged at 11,000 g for 20 minutes. The resulting pellet was homogenized in 40 volumes of 10 mM HEPES and 1 mM EGTA, pH 7.4, containing 1 mM dithiothreitol and 1 mM $MgCl_2$, and was centrifuged at 27,000 g for 20 minutes. The resulting pellet was suspended in the same buffer at a protein concentration of 1.5 mg/mL and aliquots were frozen and stored at 80° C.

$GTP\gamma^{35}S$ Binding: Assays were run in 20 mM HEPES, 100 mM NaCl, and 5 mM $MgCl_2$ at pH 7.4 in a final volume of 200 µL in 96-well Costar plates at 25° C. One hundred microliters of membrane preparation (25 µg protein per well for cell membranes and 9-15 µg per well for brain membranes) containing the appropriate concentration of GDP was added followed by addition of 50 µL of buffer±agonists and antagonists being tested followed by 50 µL of $GTP\gamma^{35}S$ to provide a final concentration in the assay of 200 pM for CHO membranes and 500 pM for brain membranes. For CHO membranes, 0.1 µM GDP was used for M1, M3, and M5 receptor assays, whereas 1 µM GDP was used for M2 and M4 assays. For brain membranes 0.1 µM GDP was used in assays carried out with anti-$G\alpha q/11$, whereas 50 µM GDP was used for assays using anti-$G\alpha i(1-3)$ and anti-$G\alpha o$. CHO cell membranes were incubated for 30 min at 25° C. with agonists and antagonists followed by addition of $GTP\gamma^{35}S$ and incubation for an additional 30 minutes. Brain membranes were incubated for 20 minutes at 25° C. with agonists and antagonists followed by addition of $GTP\gamma^{35}S$ and incubation for an additional 60 minutes. Preincubation was employed to ensure that agonists and antagonists were at equilibrium during the labeling period.

To determine total membrane binding, 50 µL of suspended wheat germ agglutinin (WGA)-coated SPA beads was added. After 15 minutes, plates were centrifuged at 1000 g for 15 minutes and radioactivity was determined using a Wallac plate counter. For determining binding to specific G proteins, $^{35}$S-labeled membranes were solubilized for 30 minutes with 0.27% Nonidet P-40 (20 µl/well of a solution containing 1.5 mL of 10% Nonidet P-40 for every 3.5 mL assay buffer) followed by addition of desired antibody (10 µL/well) to provide a final dilution of 1/400 to 1/100 and incubation for an additional 60 minutes. Fifty microliters of suspended anti-IgG-coated SPA beads was added per well, plates were incubated for 3 hours, and then were centrifuged and radioactivity determined as above. Each bottle of WGA-coated SPA beads was suspended in 10 mL of assay buffer and each bottle of anti-IgG-coated SPA beads was suspended in 20 mL of assay buffer. Protein was determined using the bicinchoninic acid assay.

Materials: $^{35}$S-GTPγS (1000-1200 Ci/mmol), anti-rabbit-IgG and anti-mouse-IgG-coated SPA beads, and WGA-coated SPA beads were obtained from Amersham (Arlington Heights, Ill.). Rabbit anti-Gαq/11 and rabbit anti-Gαi(1-3) were from Santa Cruz Biotechnologies (Santa Cruz, Calif.). Mouse monoclonal anti-Gαo was from Chemicon (Temecula, Calif.). Oxotremorine M and pirenzepine were from Research Biochemicals Inc. (Natick, Mass.). 11-{[2-((Diethylamino)methyl)-1-piperidinyl]acetyl}-5,11-dihydro-6-H-pyrido[2,3b][1,4]benzodiazepin-6-one (AFDX 116) was synthesized at Eli Lilly. Complete protease inhibitor cocktail and 10% Nonidet P-40 were from Boehringer Mannheim (Indianapolis, Ind.).

The selectivity of the M1 agonists are evaluated by screening across the other muscarinic receptor subtypes (M2, M3, M4 and M5). Compounds are also screened across a number of protein targets as well as the structurally related G protein-coupled receptor (GPCR) targets to insure selectivity for the M1 receptor.

The invention claimed is:

1. A compound of the formula

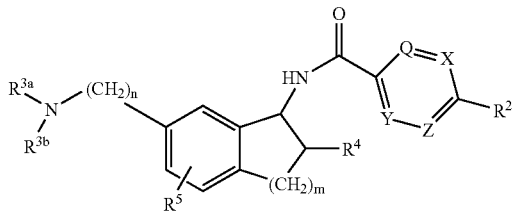

I wherein
Q, X, Y, and Z are independently selected from the group consisting of $CR^1$ and N, provided that no more than two of Q, X, Y, and Z are N and at least two of Q, X, Y, and Z are CH; or Y is CH, Z is CH, and the moiety "Q=X" represents "S" to form a thiophene ring;

$R^1$ is independently at each occurrence selected from the group consisting of hydrogen, halogen, $C_1$-$C_4$ alkoxy, and $C_1$-$C_4$ alkyl;

$R^2$ is selected from the group consisting of halogen; $C_1$-$C_4$ alkoxy; $C_1$-$C_4$ alkyl; $C_3$-$C_8$ cycloalkyl; cyano; trifluoromethyl; pyridinyl optionally substituted with one to two substituents independently selected from the group consisting of halogen, $C_1$-$C_4$ alkoxy, and $C_1$-$C_4$ alkyl; thienyl optionally substituted with one substituent selected from the group consisting of halogen, $C_1$-$C_4$ alkoxy, and $C_1$-$C_4$ alkyl; phenyl optionally substituted with from one to three substituents independently selected from the group consisting of halogen, $C_1$-$C_4$ alkoxy, $C_1$-$C_4$ alkyl, trifluoromethyl, and cyano; and pyrrolyl optionally substituted with one to two substituents independently selected from the group consisting of halogen, $C_1$-$C_4$ alkoxy, and $C_1$-$C_4$ alkyl;

$R^{3a}$ is a radical of the formula (Z')-(Y')$_q$-(')$_p$- wherein:
X' is selected from the group consisting of $C_1$-$C_4$ alkandiyl and

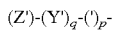

Y' is selected from the group consisting of O and S; and

Z' is selected from the group consisting of $C_1$-$C_4$ alkyl; $C_3$-$C_8$ cycloalkyl optionally substituted with one to three substituents independently selected from the group consisting of halogen, $C_1$-$C_4$ alkoxy, $C_1$-$C_4$ alkyl, trifluoromethyl, cyano, and nitro; phenyl optionally substituted with one to three substituents independently selected from the group consisting of halogen, $C_1$-$C_4$ alkoxy, $C_1$-$C_4$ alkyl, trifluoromethyl, cyano, and nitro; heteroaryl optionally substituted with one or two substituents independently selected from the group consisting of halogen, $C_1$-$C_4$ alkoxy, and $C_1$-$C_4$ alkyl; and heterocycle optionally substituted with one or two substituents independently selected from the group consisting of halogen, $C_1$-$C_4$ alkoxy, and $C_1$-$C_4$ alkyl;

p is zero or one;
q is zero or one;
provided that when p is zero, q is zero;

$R^{3b}$ is selected from the group consisting of hydrogen, $C_1$-$C_4$ alkyl, and benzyl;

or $R^{3a}$ and $R^{3b}$ are taken together with the nitrogen with which they are attached to form a heterocycle optionally substituted with one or two substituents independently selected from the group consisting of halogen, $C_1$-$C_4$ alkoxy, and $C_1$-$C_4$ alkyl;

$R^4$ is selected from the group consisting of hydrogen, hydroxy, and fluoro;

$R^5$ is selected from the group consisting of hydrogen, halogen, $C_1$-$C_4$ alkoxy, and $C_1$-$C_4$ alkyl;

m is one or two;
n is one or two;
or pharmaceutically acceptable addition salts thereof.

2. The compound of claim 1 wherein $R^5$ is hydrogen, $R^4$ is hydroxy, m is one, and which has the trans stereochemistry at the 1-and 2-position shown below:

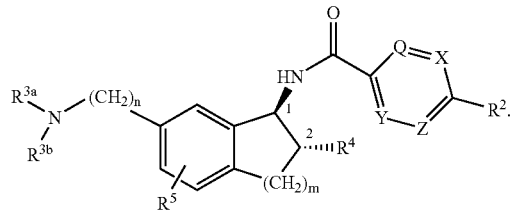

3. A compound according to claim 1 wherein Q, X, Y, and Z are each CH.

4. A compound according to claim 2 wherein Q, X, Y, and Z are each CH.

5. A compound according to claim 1 wherein one of Q, X, Y, and Z is CF and the other are CH.

6. A compound according to claim 2 wherein one of Q, X, Y, and Z is CF and the other are CH.

7. A compound according to claim 1 wherein Q is CF, and X, Y, and Z are each CH.

8. A compound according to claim 2 wherein Q is CF, and X, Y, and Z are each CH.

9. A compound according to claim 1 wherein $R^2$ is phenyl optionally substituted with from one to three substituents independently selected from the group consisting of halogen, $C_1$-$C_4$ alkoxy, $C_1$-$C_4$ alkyl, trifluoromethyl, and cyano.

10. A compound according to claim 2 wherein $R^2$ phenyl optionally substituted with from one to three substituents independently selected from the group consisting of halogen, $C_1$-$C_4$ alkoxy, $C_1$-$C_4$ alkyl, trifluoromethyl, and cyano.

11. A compound according to claim 1 wherein $R^2$ is phenyl.

12. A compound according to claim 2 wherein $R^2$ is phenyl.

13. A compound according to claim 11 wherein n is one.

14. A compound according to claim 12 wherein n is one.

15. A pharmaceutical composition comprising a compound of claim 1 and a pharmaceutically acceptable diluent.

* * * * *